US008101564B2

(12) United States Patent
Choi et al.

(10) Patent No.: US 8,101,564 B2
(45) Date of Patent: Jan. 24, 2012

(54) METHODS FOR REGULATING OSTEOCLAST DIFFERENTIATION AND BONE RESORPTION USING LRRC17

(75) Inventors: Yongwon Choi, Bryn Mawr, PA (US); Nacksung Kim, Secane, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/299,364

(22) PCT Filed: May 3, 2007

(86) PCT No.: PCT/US2007/010913
§ 371 (c)(1),
(2), (4) Date: Nov. 3, 2008

(87) PCT Pub. No.: WO2007/130619
PCT Pub. Date: Nov. 15, 2007

(65) Prior Publication Data
US 2009/0104203 A1  Apr. 23, 2009

Related U.S. Application Data

(60) Provisional application No. 60/797,236, filed on May 3, 2006.

(51) Int. Cl.
*A61K 38/00* (2006.01)
*A61K 38/16* (2006.01)
*A61K 38/17* (2006.01)
*A61K 38/18* (2006.01)
(52) U.S. Cl. ....... 514/1.1; 514/16.7; 514/16.8; 514/16.9
(58) Field of Classification Search .................... None
See application file for complete search history.

(56) References Cited

U.S. PATENT DOCUMENTS

| 5,194,596 | A | * | 3/1993 | Tischer et al. ............... 530/399 |
| 5,416,071 | A | * | 5/1995 | Igari et al. .................... 514/7.7 |
| 5,856,186 | A | | 1/1999 | Rodan et al. |
| 6,008,209 | A | * | 12/1999 | Manchand et al. ........... 514/168 |
| 6,046,030 | A | * | 4/2000 | Wu et al. ...................... 435/69.1 |
| 6,080,847 | A | * | 6/2000 | Hillman et al. ............... 536/23.5 |
| 6,096,343 | A | * | 8/2000 | Gergely et al. ............... 424/499 |
| 7,160,994 | B2 | | 1/2007 | Choi |
| 7,204,978 | B1 | * | 4/2007 | Robertson et al. ........... 424/85.1 |
| 2003/0100488 | A1 | * | 5/2003 | Boyle .............................. 514/12 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Benjamin et al., 1998, Development 125:1591-1598; see Abstract and pp. 1594-1596.*
Vukicevic et al., 1996, PNAS USA 93:9021-9026.*
Pilbeam et al., 1993, Bone 14:717-720.*

Anderson et al., "A homologue of the TNF receptor and its ligand enhance T-cell growth and dendritic-cell function," Nature 390:175179 (1997).
Arai et al., "Osteoclastogenesis-Related Antigen, a Novel Molecule on Mouse Stromal Cells, Regulates Osteoclastogenesis," J. Bone Miner. Res. 18:686-695 (2003).
Bachmann et al., "TRANCE, a Tumor Necrosis Factor Family Member Critical for CD40 Ligand-independent T Helper Cell Activation," J. Exp. Med. 189:1025-1031 (1999).
Bouxsein et al., "Ovariectomy-Induced Bone Loss Varies Among Inbred Strains of Mice," J. Bone Miner. Res. 20:1085-1092 (2005).
Boyce et al., "Requirement of pp60c-arc Expression for Osteoclasts to Form Ruffled Borders and Resorb Bone in Mice," J. Clin. Invest. 90:1622-1627 (1992).
Boyle et al., "Osteoclast differentiation and activation," Nature 423:337-342 (2003).
Brandstrom et al., "Tumor Necrosis Factor-alpha and -beta Upregulate the Levels of Osteoprotegerin mRNA in Human . . . ," Biochem. Biophys. Res. Commun. 248:454-457 (1998).
Brandstrom et al., "Regulation of Osteoprotegerin mRNA Levels by Prostaglandin E2 in Human Bone Marrow Stroma Cells," Biochem. Biophys. Res. Commun. 247:338-341 (1998).
Cella et al., "Impaired Differentiation of Osteoclasts in TREM-2-deficient Individuals," J. Exp. Med. 198:645-651 (2003).
Chen et al., "Testosterone Increases Osteoprotegerin mRNA Expression in Mouse Osteoblast Cells," Horm. Metab. Res. 36:674-678 (2004).
Chiang et al., "Interleukin-1 and Tumor Necrosis Factor Activities Partially Account for Calvarial Bone Resorption . . . ," Infect. Immun. 67:4231-4236 (1999).
Colonna, "DAP12 signaling: from immune cells to bone modeling and brain myelination," J. Clin. Invest. 111:313-314 (2003).
Feta et al., "The Osteoclast Differentiation Factor Osteoprotegerin-Ligand Is Essential for Mammary Gland Development," Cell 103:41-50 (2000).
Fox et al., "TGF-beta1 and IFN-gamma Direct Macrophage Activation by TNF-alpha to Osteoclastic or Cytocidal Phenotype," J. Immunol. 165:4957-4963 (2000).
Franzosa et al., "Requirement for NF-kappaB in osteoclast and B-cell development," Genes. Dev. 11:3482-3496 (1997).
Fuller et al., "TRANCE Is Necessary and Sufficient for Osteoblast-mediated Activation of Bone Resorption in Osteoclasts," J. Exp. Med. 188:997-1001 (1998).
Halladay et al., "Identification of Signal Transduction Pathways and Promoter Sequences That Mediate Parathyroid Hormone 1-38 Inhibition . . . ," J. Cell Biochem. 84: 1-11 (2002).
Hillier et al., "The DNA sequence of human chomosome 7," Nature 424: 157-164 (2003).
Hirotani et al., "The Calcineurin/Nuclear Factor of Activated T Cells Signaling Pathway Regulates Osteoclastogenesis . . . ," J. Biol. Chem. 279:13984-13992 (2004).

(Continued)

*Primary Examiner* — Elizabeth C Kemmerer
(74) *Attorney, Agent, or Firm* — Montgomery, McCracken, Walker & Rhoads, LLP; Evelyn H. McConathy

(57) ABSTRACT

Provided is a purified, negative regulator of osteoclast differentiation and bone resorption, specifically LRRc17. Further provided are methods and compositions for treating degenerative bone disorders, and treatments and prophylactic approaches for regulating bone resorption, and for decreasing or inhibiting the excessive bone loss associated with abnormal or excessive generation of or activity of osteoclasts.

9 Claims, 6 Drawing Sheets

OTHER PUBLICATIONS

Hofbauer et al., "Estrogen Stimulates Gene Expression and Protein Production of Osteoprotegerin in Human Osteoblastic Cells," Endocrinol. 140: 4367-4370 (1999).
Ikeda et al., "Critical roles of c-Jun signaling in regulation of NFAT family and RANKL-regulated osteoclast differentiation," J. Clin. Invest. 114:475-484 (2004).
Iotsova et al., "Osteopetrosis in mice lacking NF-kappaB1 and NF-kappaB2," Nature Medicine 3:1285-1289 (1997).
Jilka et al, "Increased Osteoclast Development After Estrogen Loss: Mediation by Interleukin-6," Science 257:88-91 (1992).
Jimi et al., "Interleukin-1alpha Activates an NF-kappaB-like Factor in Osteoclast-like Cells," J. Biol. Chem. 271:4605-4608 (1996).
Jimi et al., "Activation of NF-kappaB Is Involved in the Survival of Osteoclasts Promoted by Interleukin-1," J. Biol. Chem. 273:8799-8805 (1998).
Jimi et al., "Osteoclast Differentiation Factor Acts as a Multifunctional Regulator in Murine Osteoclast Differentiation and Function," J. Immunol. 163:434-442 (1999).
Josien et al., "TRANCE, a Tumor Necrosis Factor Family Member, Enhances the Longevity and Adjuvant Properties of Dendritic Cells In Vivo," J. Exp. Med. 191:495-501 (2000).
Kadono et al., "Strength of TRAF6 Signalling determines osteoclastogenesis," 6:171-176 (2005).
Kim et al., "A cDNA encoding a putative 37 kDa leucine-rich repeat (LRR) protein, p37NB, isolated from S-type neuroblastoma . . . ," Biochim. Biophys. Acta. 1309:183-188 (1996).
Kim et al., "Regulation of Peripheral Lymph Node Genesis by the Tumor Necrosis Factor Family Member TRANCE," J.Exp. Med. 192:1467-1478 (2000).
Kim et al., "A Novel Member of the Leukocyte Receptor Complex Regulates Osteoclast Differentiation," J.Exp. Med. 195:201-209 (2002).
Kim et al., "Diverse roles of the tumor necrosis factor family member TRANCE in skeletal physiology revealed by TRANCE . . . ," Proc. Natl. Acad. Sci. USA 97:10905-10910 (2000).
Kobayashi et al., "TRAF6 Is a Critical Factor for Dendritic Cell Maturation and Development," Immunity 19:353-363 (2003).
Koga et al., "Costimulatory signals mediated by the ITAM motif cooperate with RANKL for bone homeostatis," J. Bone Miner. Res. 428:758-763 (2004).
Kondo et al., "1alpha,25 Dihydroxyvitamin D3 Rapidly Regulates the Mouse Osteoprotegerin Gene Through Dual Pathways," J. Bone Miner. Res. 19:1411-1419 (2004).
Kong et al., "OPGL is a key regulator of osteoclastogenesis, lymphocyte development and lymph-node organogenesis," Nature 397:315-323 (1999).
Kwon et al., "TR1, a new member of the tumor necrosis factor receptor superfamily, induces fibroblast proliferation and inhibits . . . ," FASEB J. 12:845-854 (1998).
Lee et al., "Parathyroid Hormone Stimulates TRANCE and Inhibits Osteoprotegerin Messenger Ribonucleic Acid Expression in Murine Bone . . . ," Endocrinol. 140:3552-3561 (1999).
Lee et al., "Interleukin-7 Is a Direct Inhibitor of in Vitro Osteoclastogenesis," Endocrinology 144:3524-3531 (2003).
Lee et al., "1,25 (OH)2 Vitamin D3-Stimulated Osteoclast Formation in Spleen-Osteoblast Cocultures Is Mediated in Part by Enhanced . . . ," J. Immunol. 169:2374-2380 (2002).
Liu et al., "Expression and activity of osteoblast-targeted Cre recombinase transgenes in murine skeletal tissues," Int. J. Dev. Biol. 48:645-653 (2004).
Lomaga et al., "TRAF6 deficiency results in osteopetrosis and defective interleukin-1, CD40, and LPS signaling," Genes. Dev. 13:1015-1024 (1999).
Ma et al., "New Bone Formation with Teriparatide [Human Parathyroid Hormone-(1-34)] Is Not Retarded by Long-Term Pretreatment with . . . ," Endocrinology 144:2008-2015 (2003).
Massey et al., "Transforming Growth Factor-beta1 (TGF-beta) Stimulates the Osteoclast-forming Potential of Peripheral Blood Hematopoietic . . . ," Bone 28:577-582 (2001).
Matsuo et al., Nuclear Factor of Activated T-cells (NFAT) Rescues Osteoclastogenesis in Precursors Lacking c-Fos, J. Biol. Chem. 279:26475-26480 (2004).
Mocsai et al., "The immunomodulatory adapter proteins DAP12 and Fc receptor gamma-chain (FcRgamma) regulate development . . . ," Proc. Natl. Acad. Sci. USA 101:6158-6163 (2004).
Morita et al., "Plat-E: an efficient and stable system for transient packaging of retroviruses," Gene Ther. 7:1063-1066 (2000).
Murakami et al., "Transforming Growth Factor-beta1 Increases mRNA Levels of Osteoclastogenesis Inhibitory Factor . . . ," Biochem. Biophys. Res. Commun. 252:747-752 (1998).
Naito et al., "Severe osteopetrosis, defective interleukin-1 signalling and lymph node organogenesis in TRAF6-deficient mice," Genes Cells 4:353-362 (1999).
O'Brien et al., "STAT3 Activation in Stromal/Osteoblastic Cells Is Required for Induction of the Receptor Activator . . . ," J. Biol. Chem. 274:19301-19308 (1999).
Parfitt et al., "Bone Histomorphometry: Standardization of Nomenclature, Symbols, and Units," J. Bone Miner. Res. 2:595-610 (1987).
Quinn et al., "Transforming Growth Factor beta Affects Osteoclast Differentiation vis Direct and Indirect Actions," J. Bone Miner. Res. 16:1787-1794 (2001).
Rho et al., "Gene Expression Profiling of Osteoclast Differentiation by Combined Suppression Subtractive Hybridization (SSH) and cDNA . . . ," DNA Cell Biol. 21:541-549 (2002).
Rothberg et al., "slit: an extracellular protein necessary for development of midline glia and commissural axon pathways contains both EGF . . . ," Genes Dev. 4:2169-2187 (1990).
Seifert, "Abnormalities in Bone Cell Function and Endochondral Ossification in the Osteopetrotic Toothless Rat," Bone 19:329-338 (1996).
Sells Galvin et al., "TGF-beta Enhances Osteolcast Differentiation in Hematopoietic Cell Cultures Stimulated with RANKL . . . ," Biochem. Biophys. Res. Commun. 265-233-239 (1999).
Simonet et al., "Osteoprotegerin: A Novel Secreted Protein Involved in Regulation of Bone Density," Cell 89:309-319 (1997).
Sly et al., "Carbonic anhydrase II deficiency identified as the primary defect in the autosomal recessive syndrome of . . . ," Proc. Natl. Acad. Sci. USA 80:2752-2756 (1983).
Soriano et al., "Targeted Disruption of the c-src Proto-Oncogene Leads to Osteopetrosis in Mice," Cell 64:693-702 (1991).
Strausberg et al., "Generation and initial analysis of more than 15,000 full-length human and mouse cDNA sequences," Proc. Natl. Acad. Sci. USA 99:16899-16903 (2002).
Suda et al., "Modulation of Osteoclast Differentiation and Function by the New Members of the Tumor Necrosis Factor Receptor . . . ," Endocr. Rev. 20:345-357 (1999).
Takai et al., "Transforming Growth Factor-beta Stimulates the Production of Osteoprotegerin/Osteoclastogenesis Inhibitory Factor . . . ," J. Biol. Chem. 273:27091-27096 (1998).
Takami et al., "Stimulation by Toll-Like Receptors Inhibits Osteoclast Differentiation," J. Immunol. 169:1516-1523 (2002).
Takayanagi et al., "Induction and Activation of the Transcription Factor NFATc1 (NFAT2) Integrate RANKL Signaling in Terminal Differentiation . . . ," Dev. Cell 3:889-901 (2002).
Takayanagi et al., "T-cell-mediated regulation of osteoclastogenesis by signalling cross-talk between RANKL and IFN-gamma," Nature 408:600-605 (2000).
Takayanagi et al., "RANKL maintains bone homeostasis through c-Fos-dependent induction of interferon-beta," Nature 416:744-749 (2002).
Teitelbaum et al., "Osteoclasts, macrophages, and the molecular mechanisms of bone resorption," J. Leukocyte Biol. 61:381-388 (1997).
Teitelbaum, "Bone Resorption by Osteoclasts," Science 28:1504-1508 (2000).
Thirunavukkarasu et al., "The Osteoblast-specific Transcription Factor Cbfa1 Contributes to the Expression of Osteoprotegerin . . . ," J. Biol. Chem. 275:25163-25172 (2000).
Thirunavukkarasu et al., "Stimulation of Osteoprotegerin (OPG) Gene Expression by Transforming Growth Factor-beta (TGF-beta)," J. Biol. Chem. 276:36241-36250 (2001).

Tondravi et al., "Osteopetrosis in mice lacking haematopoietic transcription factor PU.1," Nature 386:81-84 (1997).

Vidal et al., "Osteoprotegerin mRNA Is Increased by Interleukin-1alpha in the Human Osteosarcoma Cell Line MG-63 . . . ," Bichem. Biophys. Res. Commun. 248:696-700 (1998).

Visnjic et al., "Hematopoiesis is severely altered in mice with an induced osteoblast deficiency," Blood 103:3258-3264 (2004).

Visnjic et al., "Conditional Ablation of the Osteoblast Lineage in Col2.3Deltatk Transgenic Mice," J. Bone Miner. Res. 16:2222-2231 (2001).

Walsh et al., "Biology of the TRANCE axis," Cytokine Growth Factor Rev. 14:251-263 (2003).

Wang et al., "Bone and haematopoietic defects in mice lacking c-fos," Nature 360:741-745 (1992).

Wiktor-Jedrzejczak et al., "Total absence of colony-stimulating factor 1 in the macrophage-deficient osteopetrotic (op/op) . . . ," Proc. Natl. Acad. Sci. USA 87:4828-4832 (1990).

Wong et al., "TRANCE Is a Novel Ligand of the Tumor Necrosis Factor Receptor Family That Activates c-Jun N-terminal Kinase T Cells," J. Bio. Chem. 272:25190-25194 (1997).

Yamamoto et al., "Bone Marrow-derived Osteoclast-like Cells from a Patient with Craniometaphyseal Dysplasia Lack Expression . . . ," J. Clin. Invest. 91:362-367 (1993).

Yang et al., "Muramyl Dipeptide Enhances Osteoclast Formation Induced by Lipopolysaccharide, IL-1alpha, and TNF-alpha through Nucleotide . . . ," J. Immunol. 175:1956-1964 (2005).

Yasuda et al., "Identity of Osteoclastogenesis Inhibitory Factor (OCIF) and Osteoprotegerin (OPG): a Mechanism by which OPG/OCIF . . . ," Endocrinology 139:1329-1337 1998).

Yasuda et al., "Osteoclast differentiation factor is a ligand for osteoprotegerin/osteoclastogenesis-inhibitory . . . ," Proc. Natl. Acad. Sci. USA 95:3597-3602 (1998).

Yoshida et al., "The murine mutation osteopetrosis is in the coding region of the macrophage colony stimulating factor gene," Nature 345:442-444 (1990).

Yun et al., "OPG/FDCR-1, a TNF Receptor Family Member, Is Expressed in Lymphoid Cells and Is Up-Regulated by Ligating CD401," J. Immunol. 16:6113-6121 (1998).

Zhang et al., "Osteoblast-specific Knockout of the Insulin-like Growth Factor (IGF) Receptor Gene Reveals an Essential Role of IGF . . . ," J. Biol. Chem. 277:44005-44012 (2002).

Colonna, "Trems in the Immune System and Beyond," Nat. Rev. Immunol. 3:445-453 (2003).

Gelb et al., "Pycnodysostosis, a Lysosomal Disease Caused by Cathepsin K Deficiency," Science 273:1236-1238 (1996).

Grigoriadis et al., "c-Fos: A Key Regulator of Osteoclast-Macrophage Lineage Determination and Bone Remodeling," Science 266:443-448 (1994).

Hofbauer et al., "Interleukin-1beta and Tumor Necrosis Factor-alpha, But Not Interleukin-6, Stimulate Osteoprotegerin ligand Gene . . . ," Bone 25:255-259 (1999).

Josien et al., "TRANCE, a TNF Family Member, Is Differentially Expressed on T Cell Subsets and Induces Cytokine Production in Dendritic Cells," J. Immunol. 2562-2568 (1999).

Kalu et al., "The Aged Rat Model of Ovarian Hormone Deficiency Bone Loss," Endocrinology 124:7-16 (1989).

Kim et al., "Osteoclast differentiation independent of the TRANCE-RANK-TRAF6 axis," J. Exp. Med. 202:589-595 (2005).

Kimble et al., "Estrogen Deficiency Increases the Ability of Stromal Cells to Support Murine Osteoclastogenesis via an . . . ," J. Biol. Chem. 271:28890-28897 (1996).

Niwa et al., "Efficient selection for high-expression transfectants with a novel eukaryotic vector," Gene 1991:193-199 (1991).

Odgren et al., "The Toothless Osteopetrotic Rat Has a Normal Vitamin D-Binding Protein-Macrophage Activating Factor (DBP-MAF) Cascade and . . . ," Bone 25:175-181 (1999).

Safadi et al., "Skeletal Resistance to 1,25-Dihydroxyvitamin D3 in Osteopetrotic Rats," Endocrine 11:309-319 (1999).

Suda et al., "Role of 1alpha, 25-Dihydroxyvitamin D3 in Osteoclast Differentiation and Function," Methods Enzymol. 282:223-235 (1997).

Tan et al., "Characterization of a novel TNF-like ligand and recently described TNF ligand and TNF receptor superfamily genes and their . . . ," Gene 204:35-46 (1997).

Lacey et al., "Osteoprotegerin Ligand Is a Cytokine that Regulates Osteoclast Differentiation and ACtivation," Cell 93:165-176 (1998).

Linhart et al., "Deciphering Transcriptional Regulatory Elements that Encode Specific Cell Cycle Phasing by Comparative Genomics Analysis," Cell Cycle 4(12):1788-1797 (2005).

* cited by examiner

```
  1 MRIVAILLLF CLCRAAEPRK SSPGVLRSQG NPSRSHGRGG RRGSSPVKRY
    Signal peptide
 51 APGLPCDVYT YLHEKYLDCQ ERKLVYVLPD WPQDLLHMLL ARNKIRVLKN 101 NMFAKEKRLK SLDLQQNEIS KIESEAFFGL NKLTTLLLQH NQIKVLTEEA
             LRR1                          LRR2
151 FIYTPLLSYL RLYDNPWHCT CELETLISML QIPRNRNLGN YAKCGSPPAL

201 RNKKLLQLKP QELCDEEEKE QLDPKPQVSG IPAVIRPEAD STLCHNYVFP

251 IQTLDCKRKE LKKVPSNIPP DIVKLDLSSN KIRQLRPKEF EDVHELKKLN
                                LRR3
301 LSSNGIEFID PAAFLGLIHL EELDLSNNSL QNFDYGVLED LYFLKLLWLR
      LRR4                  LRR5
351 DNPWRCDYSI HYLYYWIKHH YNVHYNGLEC KTPEEYKGWS VGKYVRSYYE

401 ECPKDKLPAY PETFDQDTED DEWQKIHRDH PAKKHRVRIT IVG
```

FIG. 4

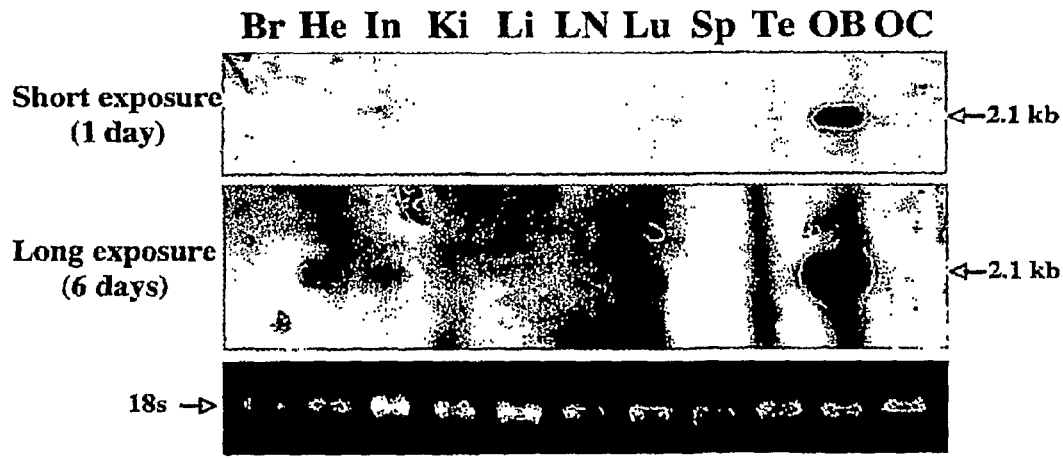

FIG. 5

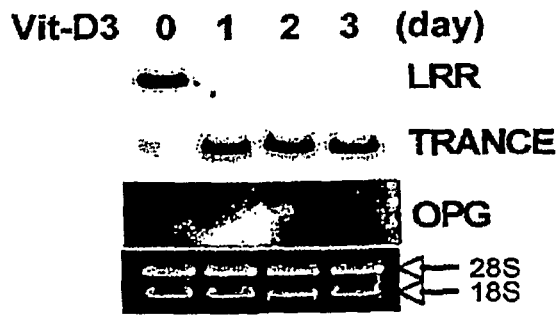
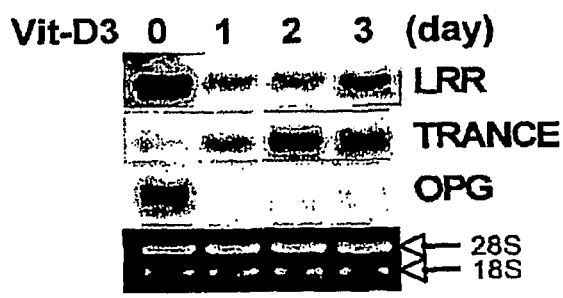
FIG. 6
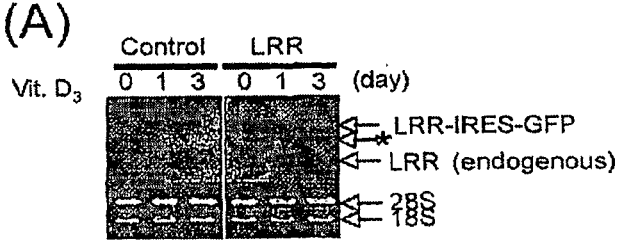
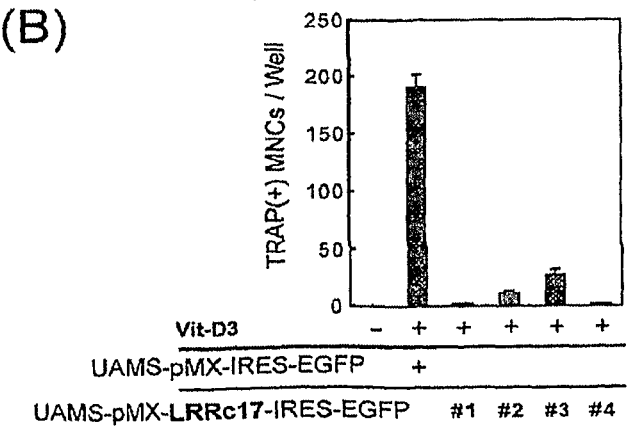
FIG. 7

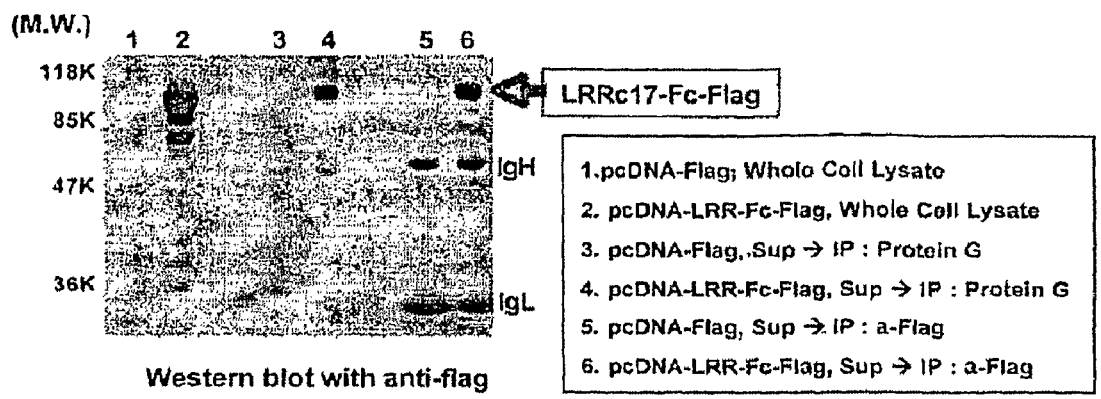
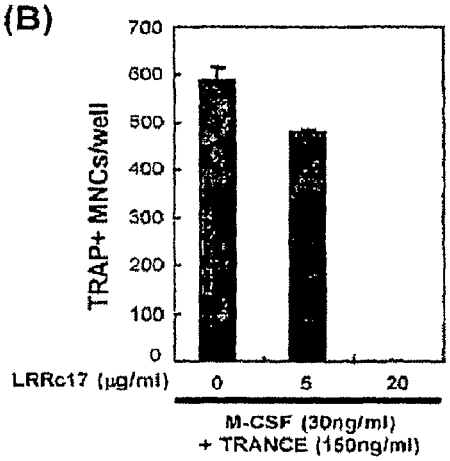
FIG. 10

SEQUENCE LISTING

<160> NUMBER OF SEQ ID NOS: 3

<210> SEQ ID NO 1
<211> LENGTH: 443
<212> TYPE: PRT
<213> ORGANISM: Homo sapiens

```
<400> SEQUENCE: 1

Met Arg Ile Val Ala Ile Leu Leu Phe Cys Leu Cys Arg Ala Ala
1               5                   10                  15

Glu Pro Arg Lys Ser Ser Pro Gly Val Leu Arg Ser Gln Gly Asn Pro
            20                  25                  30

Ser Arg Ser His Gly Arg Gly Gly Arg Arg Gly Ser Ser Pro Val Lys
        35                  40                  45

Arg Tyr Ala Pro Gly Leu Pro Cys Asp Val Tyr Thr Tyr Leu His Glu
    50                  55                  60

Lys Tyr Leu Asp Cys Gln Glu Arg Lys Leu Val Tyr Val Leu Pro Asp
65                  70                  75                  80

Trp Pro Gln Asp Leu Leu His Met Leu Leu Ala Arg Asn Lys Ile Arg
                85                  90                  95

Val Leu Lys Asn Asn Met Phe Ala Lys Phe Lys Arg Leu Lys Ser Leu
            100                 105                 110

Asp Leu Gln Gln Asn Glu Ile Ser Lys Ile Glu Ser Glu Ala Phe Phe
        115                 120                 125

Gly Leu Asn Lys Leu Thr Thr Leu Leu Leu Gln His Asn Gln Ile Lys
    130                 135                 140

Val Leu Thr Glu Glu Ala Phe Ile Tyr Thr Pro Leu Leu Ser Tyr Leu
145                 150                 155                 160

Arg Leu Tyr Asp Asn Pro Trp His Cys Thr Cys Glu Leu Glu Thr Leu
                165                 170                 175

Ile Ser Met Leu Gln Ile Pro Arg Asn Arg Asn Leu Gly Asn Tyr Ala
            180                 185                 190

Lys Cys Gly Ser Pro Pro Ala Leu Arg Asn Lys Lys Leu Leu Gln Leu
        195                 200                 205

Lys Pro Gln Glu Leu Cys Asp Glu Glu Lys Glu Gln Leu Asp Pro
    210                 215                 220

Lys Pro Gln Val Ser Gly Ile Pro Ala Val Ile Arg Pro Glu Ala Asp
225                 230                 235                 240

Ser Thr Leu Cys His Asn Tyr Val Phe Pro Ile Gln Thr Leu Asp Cys
                245                 250                 255

Lys Arg Lys Glu Leu Lys Lys Val Pro Ser Asn Ile Pro Pro Asp Ile
            260                 265                 270

Val Lys Leu Asp Leu Ser Ser Asn Lys Ile Arg Gln Leu Arg Pro Lys
        275                 280                 285

Glu Phe Glu Asp Val His Glu Leu Lys Lys Leu Asn Leu Ser Ser Asn
    290                 295                 300

Gly Ile Glu Phe Ile Asp Pro Ala Ala Phe Leu Gly Leu Ile His Leu
305                 310                 315                 320

Glu Glu Leu Asp Leu Ser Asn Asn Ser Leu Gln Asn Phe Asp Tyr Gly
                325                 330                 335

Val Leu Glu Asp Leu Tyr Phe Leu Lys Leu Leu Trp Leu Arg Asp Asn
            340                 345                 350

Pro Trp Arg Cys Asp Tyr Ser Ile His Tyr Leu Tyr Tyr Trp Leu Lys
        355                 360                 365

His His Tyr Asn Val His Tyr Asn Gly Leu Glu Cys Lys Thr Pro Glu
    370                 375                 380

Glu Tyr Lys Gly Trp Ser Val Gly Lys Tyr Val Arg Ser Tyr Tyr Glu
385                 390                 395                 400

Glu Cys Pro Lys Asp Lys Leu Pro Ala Tyr Pro Glu Thr Phe Asp Gln
                405                 410                 415
```

-continued

```
Asp Thr Glu Asp Asp Glu Trp Gln Lys Ile His Arg Asp His Pro Ala
            420                 425                 430
Lys Lys His Arg Val Arg Ile Thr Ile Val Gly
        435                 440

<210> SEQ ID NO 2
<211> LENGTH: 36
<212> TYPE: DNA
<213> ORGANISM: Artificial
<220> FEATURE:
<223> OTHER INFORMATION: Synthetic

<400> SEQUENCE: 2
agatctctgg aagttctgtt ccagggggcc ggatct                                36

<210> SEQ ID NO 3
<211> LENGTH: 8
<212> TYPE: PRT
<213> ORGANISM: Artificial
<220> FEATURE:
<223> OTHER INFORMATION: Synthetic

<400> SEQUENCE: 3

Leu Glu Val Leu Phe Gln Gly Pro
1               5
```

METHODS FOR REGULATING OSTEOCLAST DIFFERENTIATION AND BONE RESORPTION USING LRRC17

CROSS REFERENCE TO RELATED APPLICATIONS

This application claims priority to U.S. Provisional Application No. 60/797,236, filed May 3, 2006, and PCT/US2007/010913, filed May 3, 2007, which are each incorporated herein in its entirety.

GOVERNMENT INTEREST

This invention was supported in part by Grant No. 10053453 from the Department of Health and Human Services. Accordingly, the Government may have certain rights in this invention.

FIELD OF THE INVENTION

The present invention relates to regulating osteoclast differentiation and bone resorption, specifically as related to LRRc17.

BACKGROUND OF THE INVENTION

Bones provide rigid support for the body, mechanical integrity of movement and protection, and serve as a site of mineral homeostasis. Additionally, bone is an indispensable connective tissue and the primary site for hematopoiesis. Bone is continuously remodeled through new bone formation by osteoblast cells and by resorption of old bone by osteoclast cells, a renewal process which provides the skeleton with structural and functional integrity (Boyle et al., *Nature* 423:337-342 (2003); Teitelbaum, *Science* 289:1504-1508 (2000); Suda et al., *Endocr. Rev.* 20:345-357 (1999); Stein et al., In *Principles of Bone Biology*. (Bilezikian, Raisz, Rodan, eds.) Academic Press (1996)). Thus, bone remodeling occurs through the coupled actions of osteoblasts and osteoclasts.

Fresh layers of osteoid, a cement-like substance, are spread down onto existing bone by osteoblasts. Bone formation is completed when hyroxyapatite crystals are deposited on the osteoid. Osteoclasts, the primary cells responsible for bone resorption, arise from hematopoietic cells of the macrophage/monocyte lineage and are multinucleated cells (i.e., polykaryons) that form by fusion of monocytes. Osteoclasts adhere to bone and remove it by acidification and proteolytic digestion. Tunnels are then formed in the bone, and the tunnels function as pathways for osteoblasts and small blood vessels. New layers of osteoid are deposited inside the tunnels and this eventually becomes new bone matrix (Boyle et al., supra, 2003; Teitelbaum, supra, 2000; Suda et al., supra, 1999; Stein et al., supra, 1996). Bone homeostasis is, thus, also maintained by coupled actions of osteoblasts and osteoclasts.

Despite being derived from the same bone marrow precursor cells of the monocyte-macrophage lineage that give rise to macrophages and dendritic cells, osteoclasts are the only cells capable of resorbing bone (Boyle et al., supra, 2003; Teitelbaum, supra, 2000; Suda et al., supra, 1999). The differentiation of osteoclasts from myelomonocytic precursors is tightly regulated and supported by the activity of osteoblasts. Hence, many of the osteotropic factors modulating osteoclast differentiation have been identified and are shown to exert their actions by regulating osteoblasts.

Through the study of various spontaneous and induced mutant mice, there has been considerable progress made in the field of osteoclast development. Osteoclasts secrete various enzymes that act in dissolution of bone material. For example, tartrate resistant acid phosphatase (TRACP) decalcifies the bone, while cathepsin K digests the bone matrix proteins. Osteoclasts also acidify the surrounding environment through vacuolar $H^+$-ATPase activity, thereby further promoting bone disruption. Other cell-autonomous factors for osteoclast differentiation have been identified using various knockout mice. c-Fos KO mice also fail to generate osteoclasts, and thus become osteopetrotic, but they produce macrophages (Wang et al., *Nature* 360:741-745 (1992); Grigoriadis et al., *Science* 266:443-448 (1994)). Mice lacking both p50 and p52 subunits of NF-κB display defects in osteoclast development similar to those seen in c-Fos KO mice (Iotsova et al., *Nat. Med.* 3:1285-1289 (1997); Franzoso et al., *Genes Dev.* 11:3482-3496 (1997)).

Osteoblasts induce osteoclastogenesis from bone marrow precursors, and the process is influenced by various cells producing osteotropic factors that modulate bone homeostasis. These factors can be divided into three groups: 1) those influencing the activity of osteoblasts (e.g., parathyroid hormone (PTH) or 1,25-dihydroxyvitamin DS $(1,25(OH)_2D_3$ [referred to herein as "Vit-D3"] regulating the expression of TRANCE in osteoblasts); 2) those affecting osteoclast precursors or osteoclasts per se (e.g., the putative ligands for OSCAR or TREM); and 3) those with bipotential effects (e.g., TGF-β can either inhibit or promote osteoclast differentiation by acting on osteoblasts or osteoclasts, respectively). Osteoblasts provide at least two factors required for osteoclastogenesis, TRANCE (TNF [tumor necrosis factor]-related activation-induced cytokine) and M-CSF (mononuclear phagocyte colony-stimulating factor), as well as a critical inhibitory factor, OPG (osteoprotegerin).

In addition, factors from osteoblasts have also been shown to be essential for osteoclast differentiation. The osteoblast protein RANKL (receptor for activating NF-κB ligand) also called osteoclast differentiation factor (ODF) (Yasuda et al., *Proc. Natl. Acad. Sci. USA* 95:3597-3602 (1998b), osteoprotegerin ligand (OPGL) (Lacey et al., *Cell* 93:165-176 (1998)), or TRANCE (Wong et al., *J. Bio. Chem.* 272:25190-25194 (1997)), is a cytokine belonging to the TNF (tumor necrosis factor) family (Anderson et al., *Nature* 390:175-179 (1997)). "RANK" refers to TRANCE/RANK, and "OPG" refers to OPG/OCIF/TR1/FDCR-1, (Simonet et al., *Cell*, 89:309-319, (1997); Yasuda et al., *Endochronol.* 139:1329-1337 (1998a); Tan et al., *Gene* 204:35-46 (1997); Kwon et al., *FASEB J.* 12:845-854, (1998); Yun et al., *J. Immunol.* 161:6113-6121 (1998), based on the chronological order of publication.) For simplicity, therefore, the term "TRANCE" refers herein to "TRANCE/RANKL/OPGL/ODF.").

TRANCE is a key regulator that stimulates differentiation of osteoclast precursor cells and activates mature osteoclasts. Thus, it plays a major role in homeostasis of the bone by inducing differentiation (Lacey et al., supra, 1998) and the osteoblast-mediated activation of bone resorption by osteoclasts (Fuller et al., supra, 1998; Jimi et al., *J. Immunol.* 163:434-442 (1999). It also inhibits apoptosis of osteoclasts (Fuller et al., *J. Exp. Med.* 188:997-1001 (1998)). These functions of TRANCE/RANKL/OPGL/ODF are mediated by binding to its receptor, RANK (receptor activator of NF-κB). In vivo, the direct role of TRANCE in osteoclastogenesis, and osteoclast differentiation has been demonstrated by, e.g., Kim et al., *Proc. Natl. Acad. Sci. USA* 97:10905-10910 (2000), and Kong et al., *Nature* 397:315-323 (1999).

Recent findings also show that the expression of TRANCE and optimal TRANCE-induced osteoclast differentiation and bone-resorbing activity requires the action of various bone resorbing hormones (e.g., Vit-D3 or PTH) and co-stimulatory receptors (e.g., OSCAR or TREM), and additional soluble factors, such as inflammatory cytokines (e.g., IL-1, IL-6, IL-11 and TNF-α), glucocorticoids, and parathyroid hormone (PTH). Calcitonin, and prostaglandin E2 also regulate osteoclast activity (Boyle et al., supra, 2003; Teitelbaum, supra, 2000; Suda et al., supra, 1999). Moreover, that the action of TRANCE on osteoclast precursors in osteoclast differentiation is potentiated by additional cytokines and co-stimulatory factors (e.g., IL-1, TNF-β, and the putative ligands for OSCAR or TREM), and counteracted upon by inhibitory molecules (e.g., GM-CSF, INF-γ and INF-β) (Boyle et al., supra, 2003; Teitelbaum, supra, 2000; Suda et al., supra, 1999; Koga et al., *Nature* 428:758-763 (2004); Mocsai et al., *Proc. Natl. Acad. Sci. USA* 101:6158-6163 (2004); Kim et al., *J. Exp. Med.* 195:201-209 (2002); Cella et al., *J. Exp. Med.* 198:645-651 (2003); Colonna, *Nat. Rev. Immunol.* 3:445-453 (2003); Colonna, *J. Clin. Invest.* 111: 313-314 (2003); Jimi et al., *J. Biol. Chem.* 271:4605-4608 (1996); Jimi et al., *J. Biol. Chem.* 273:8799-8805 (1998); Takayanagi et al., *Nature* 408:600-605 (2000); Fox et al., *J. Immunol.* 165:4957-4963 (2000); Sells Galvin et al., *Biochem. Biophys. Res. Commun.* 265:233-239 (1999); Massey et al., *Bone* 28:577-582 (2001); Takayanagi et al., *Nature* 416:744-749 (2002); Lee et al., *Endocrinol.* 144:3524-3531 (2003)).

Thus, the presence of TRANCE up-regulators leads to enhanced bone resorption and a corresponding loss of bone mass, further indicating that TRANCE, like M-CSF, is one of the factors provided by osteoblasts for osteoclast differentiation. In addition, when recombinant M-CSF and TRANCE are added to bone marrow cells or spleen cells in culture they differentiate into bone-resorbing mature osteoclasts, even in the absence of osteoblasts/stromal cells. TRANCE KO mice are osteopetrotic due to defects in osteoclast development, although TRANCE KO mice have normal macrophages.

Osteoblasts also produce a decoy ligand, osteoprotegrin (OPG), which competes with TRANCE and inhibits its activity. OPG production is up-regulated by cytokines IL-1 and TNF-α, steroid hormone β-estradiol, and mechanical stress, thereby stimulating bone formation. In contrast, gluococorticoids, PTH, and prostaglandins suppress production of OPG, while enhancing the expression of TRANCE, and thus, enhance bone resorption. Thus, the net effect of pro-osteoclastogenic factors on osteoblasts is, in general, to increase the ratio between TRANCE and OPG, maximizing the capacity of activated osteoblasts to induce osteoclast differentiation (Boyle et al., supra, 2003; Teitelbaum, supra, 2000; Suda et al., supra, 1999; Lee et al., *J. Immunol.* 169:2374-2380 (2002); Lee et al., *Endocrinol.* 140:3552-3561 (1999); Kimble et al., *J. Biol. Chem.* 271:28890-28897 (1999); Thirunavukkarasu et al., *J. Biol. Chem.* 275:25163-25172. (2000); Thirunavukkarasu et al. *J. Biol. Chem.* 276: 36241-36250 (2001); Halladay et al., *J. Cell Biochem.* 84:1-11 (2001); Kondo et al., *J. Bone. Miner. Res.* 19:1411-1419 (2004); Quinn et al., supra, 2001; Takai et al., supra, 1998; Brandstrom et al., *Biochem. Biophys. Res. Commun.* 247: 338-341 (1998); Brandstrom et al., *Biochem. Biophys. Res. Commun.* 248:454-457 (1998); Chen et al., *Horm. Metab. Res.* 36:674-678 (2004); Hofbauer et al., *Endocrinol.* 140: 4367-4370 (1999); Vidal et al., *Biochem. Biophys. Res. Commun.* 248:696-700 (1998); Nakamichi et al., *J. Immunol.* 175: 1956-1964 (2005)).

Although elucidation of pro-osteoclastogenic factors produced by osteoblasts in response to bone resorbing hormones has progressed considerably in recent years, the characterization of inhibitory factors that are produced in osteoblasts, but suppressed by pro-osteoclastogenic factors has been more limited. OPG expression is suppressed in osteoblasts in response to pro-osteoclastogenic factors, although OPG is indeed a critical inhibitor that should be suppressed to promote osteoclastogenesis. Thus, it is possible that other osteoblastic inhibitors exist. For example, the anti-osteoclastogenic action of TGF-β in the osteoblast-induced osteoclast differentiation system in vitro cannot be fully reversed by anti-OPG (Takai et al., *J. Bio. Chem.* 273:27091-27096 (1998); Murakami et al., *Biochem. Biophys. Res. Commun.* 252:747-752 (1998). Moreover, even when OPG-deficient osteoblasts are used in a co-culture system, TGF-β still exerts its anti-osteoclastogenic action (Quinn et al., *J. Bone Mineral Res.* 16:1787-1794 (2001), suggesting that additional inhibitory factors are produced by osteoblasts.

Moreover, when mature osteoclasts attach to the bone surface, a characteristic resorption pit forms below the cell at the site of attachment of the ruffled border (Boyle et al., supra, 2003; Teitelbaum, supra, 2000; Suda et al., supra, 1999). The specialized ruffled border and sealing zone appear only in activated osteoclasts during bone resorption. Mature osteoclasts express various molecules involved in bone resorption, such as carbonic anhydrase II, integrins, $H^+$-ATPase-type proton pump, and several proteases, including cathepsins (Boyle et al., supra, 2003; Teitelbaum, supra, 2000; Suda et al., supra, 1999). In humans, mutations in carbonic anhydrase II, $H^+$-ATPase-type proton pump, and cathepsin K have been associated with defective bone resorption by osteoclasts, indicating that these molecules are important regulators of OC function Sly et al., *Proc. Natl. Acad. Sci. USA*, 80:2752-2756 (1983); Yamamoto et al., *J. Clin. Invest.* 91:362-367 (1993); Gelb et al., *Science* 273:1236-1238 (1996)).

Until the present invention, only limited progress had been made in determining the nature of such inhibitors. The question of whether other osteoblast-produced inhibitors are regulated like OPG expression in response to osteotropic factors or whether their regulation contributes to the mechanisms of bone homeostasis regulated by osteotropic factors remained unanswered. It is, however, likely that additional molecules, yet-to-be identified, are differentially produced by osteoblasts in response to various osteotropic factors, either to promote or inhibit osteoclast differentiation. In addition, expression of some factors may need to be regulated coordinately with TRANCE or OPG in osteoblasts for proper bone homeostasis. Further elucidation of such molecules that mediate the communication between osteoblasts and osteoclasts is required to fully understand how bone homeostasis is maintained, and to develop better therapeutics for various diseases in bone.

Thus, there remains a need in the art for the identifying and further characterizing additional co-stimulators and inhibitors, which is crucial for understanding how osteoclast differentiation is regulated. Since osteoclasts are the principal, if not the only, cells which can resorb bone, understanding the molecular pathways leading to the differentiation and activation of osteoclasts will improve the treatment of arthritis and degenerative bone diseases resulting in excessive bone resorption.

SUMMARY OF THE INVENTION

The present invention relates to regulating osteoclast differentiation and bone resorption, specifically as related to LRRc17, and provides methods and compositions for treating degenerative bone disorders, as well as treatments and prophylactic approaches for regulating bone resorption, and for decreasing or inhibiting the excessive bone loss associated with abnormal activity of osteoclasts. To provide insight into how osteotropic factors regulate osteoclast differentiation by modulating osteoblast activity, mRNA expression profiles of osteoblasts stimulated with Vit-D3 were compared with the effect in fibroblasts. By PCR-select cDNA subtraction cloning, a member was identified of the Leucine Rich Repeat (LRR) proteins, LRRc17 (LRR containing 17), of previously unknown function, whose expression is highly enriched in osteoblasts compared to fibroblasts. LRR proteins are characterized by short leucine-rich repeats (LRRs) of 22-28 residues in length with LxxLxLxxN/CxL consensus sequences. The LRR motifs can be found in various cytoplasmic, membrane and extracellular proteins (e.g., toll-like receptors) Rothberg et al., Genes Dev. 4:2169-2187, (1990). Although these proteins are associated with widely varied functions, a common property of LRR proteins is involvement in protein-protein interactions.

In the present invention, LRRc17 mRNA expression in osteoblasts was suppressed by the pro-osteoclastogenic factor Vit-D3. Moreover, upon Vit-D3 stimulation, the expression of LRRc17 mRNA displayed an inverse correlation with that of TRANCE, which is up-regulated in osteoblasts to promote osteoclast differentiation. In addition, as shown in the present invention, if LRRc17 expression is enforced in osteoblasts, Vit-D3 activation fails to induce osteoclast differentiation, leading to the characterization of LRRc17 as an important negative regulator of osteoclast differentiation produced in osteoblasts.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

FIG. 4 provides the predicted amino acid sequence of LRRc17 (SEQ ID No:1).

FIG. 5 is an image of a Northern blot analysis showing LRRc17 expression. Br=OC=bone marrow osteoclasts.brain; He=heart; In=intestine; Ki=kidney; Li=liver; LN=lymph node; Lu=lung; Sp=spleen; Te=testis; OB=calvarial osteoblasts;

FIGS. 6A and 6B are images of Northern blots showing a comparison of LRRc17 mRNA expression levels to that of TRANCE and OPG mRNA in osteoblasts. FIG. 6A shows a comparison in cells of the UAMS-32 osteoblastic cell line. FIG. 6B shows a comparison in mouse primary calvarial osteoblasts.

FIGS. 7A and 7B demonstrate that constitutive expression of LRRc17 inhibits osteoblast-mediated osteoclast differentiation in response to Vit-D3. FIG. 7A is an image of a Northern blot of DAMS cells transfected with control (pMX-IRES-EGFP) or LRR expression vector (pMX-LRRc17-IRES-EGFP), and then stimulated with Vit-D3, followed by Northern analysis using LRRc17 cDNA. Unlike endogenous LRRc17, LRRc17-IRES-EGFP mRNA persisted even after Vit-D3 stimulation. The star (*) in FIG. 7A appears to be a breakdown of the full-length LRR-IRES-GFP mRNA. FIG. 7B is a graph showing osteoclast differentiation induced by Vit-D3 in the co-culture system with UAMS transfectants.

FIGS. 10A and 10B show the LRRc17-Fc-Flag fusion protein in a transient transfection system. FIG. 10A is an image of a western blot analysis of purified LRRc17 protein. FIG. 10B is a graph showing the inhibition of osteoclast differentiation by LRRc17. Data are from a single experiment with triplicates for each condition.

Figure 1:
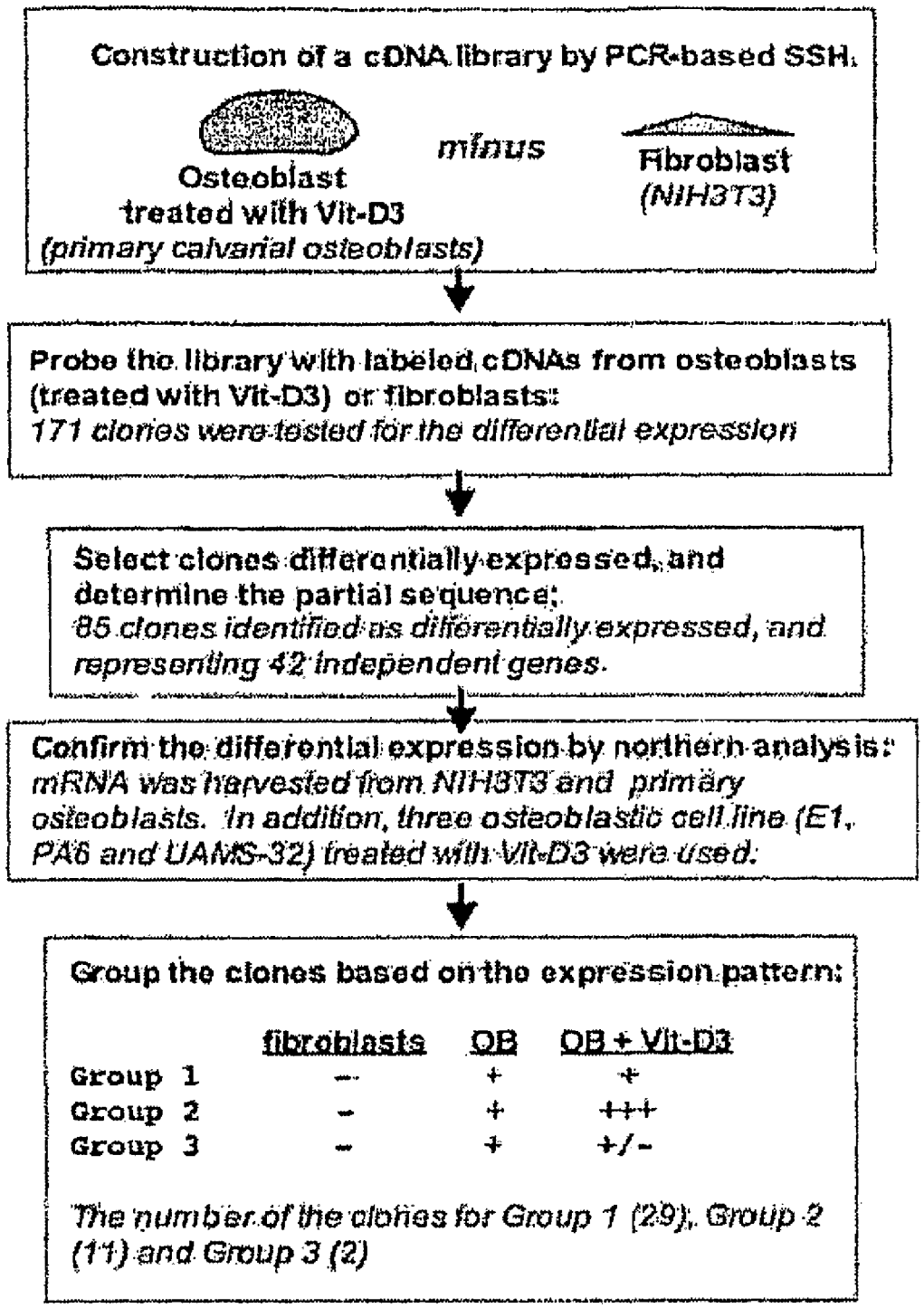
FIG. 1 provides a schematic of the experimental design of the invention.

DESCRIPTION OF PREFERRED
EMBODIMENTS OF THE INVENTION

The present invention provides methods and compositions for directly regulating osteoclast differentiation and bone resorption. Specifically, LRRc17 is one of the critical inhibitors that modulate osteoblast-induced osteoclast differentiation, and it has been demonstrated herein that certain osteotropic factors exert their actions by regulating the production and/or activity of LRRc17 in osteoblasts. The present disclosure further provides methods and compositions for treating degenerative bone disorders, as well as treatments and prophylactic approaches for regulating bone resorption, and for decreasing or inhibiting the excessive bone loss associated with abnormal activity of osteoclasts. In addition, in those degenerative bone disorders where inappropriate remodeling results in compromised bone integrity, albeit without significant bone loss, the regulation of osteoclast differentiation and activity and inhibition of bone resorption can increase bone strength sufficiently to decrease the fracture risk. As embodied herein, bone homeostasis is maintained by the balanced activities of matrix-producing osteoblasts and bone-resorbing osteoclasts.

Bone remodeling is a complex process, tightly regulated by the balanced action of osteoblasts and osteoclasts. Osteoclasts are multinucleated, giant cells of hematopoietic origin and are formed by the fusion of mononuclear pre-osteoclasts derived from myeloid lineage cells. During normal physiological conditions, osteoclastogenesis is mainly controlled by osteoblast-produced molecules induced by various osteotropic factors. To grow or maintain bone mass, there must be an appropriate balance in the rates of bone formation and bone resorption. Any abnormal imbalance between the two processes, such as excessive bone remodeling or a net excess of bone resorption over bone formation, can lead to adverse changes in the bone structure.

In the present invention, various degenerative bone disorders can be treated by administering to a subject in need thereof an amount of OB86 or an LRRc17 inhibitory compound, such as Vit-D3, in a therapeutically effective amount to treat an osteoclast imbalance, otherwise resulting in the bone disorder. The term "subject" refers herein to a mammal, including a human in need of therapy for, or susceptible to, a condition or its sequelae. The subject may include dogs, cats, pigs, cows, sheep, goats, horses, rats, and mice and humans. The term "subject" does not exclude an individual that is normal in all respects. The diagnosis of a particular disorder can be based on clinical presentations typically used by those skilled in the art to diagnose the disorder. As further discussed herein, other diagnostic criteria such as the presence of biochemical and molecular markers of the disease, can be used independently or as a supplement to the examination of the clinical presentations. Standard diagnostic criteria can be found in various references, including, e.g., without limitation, the World Health Organization's International Classification of Diseases, Tenth Revision (ICD-10).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

As used herein, "bone formation" and "bone deposition" refer to the process of laying down of new bone material. The osteoblast is the primary cell responsible for forming the bone organic matrix and incorporation of hydroxyapatite crystals during mineralization of the matrix. As such, bone formation encompasses the synthesis of the organic matrix and the mineralization process involving incorporation of hydroxyapatite.

A "bone modulating agent" refers to a compound or composition capable of altering bone loss, changing bone mass, and/or modifying bone structural integrity (i.e., strength of bone) by permitting bone rejuvenation resulting in new bone deposition. Bone modulating agents encompass resorptive agents and osteogenic agents. The classification of agents in one group or the other reflects the current state of knowledge about the properties of the agents in relation to bone metabolism and is not meant to limiting. "Bone resorption" refers to the process of bone removal or dissolution.

"Bone mineral density" or "bone density" or "BMD" refers to the bone mass in a given area or volume of bone, and is used as a measure of bone health and in the diagnosis of degenerative bone disorders. As is known in the art, the bone mineral density is dependent on the procedure used to determine bone density. Mass per area refers to real bone mineral density and is generally expressed in $gm/cm^2$. DEXA and ultrasound are examples of bone density measurement techniques. Mass per volume is a volumetric bone mineral density and is generally expressed in $gm/cm^3$. Quantitative computed tomography and magnetic resonance imaging are examples of volumetric bone density measurement techniques. Because the bone mineral density varies with the technique used, the density measurements are translated into "T" and "Z" scores as defined by the World Health Organization (WHO). The T-score is a comparison of a subject's bone mineral density to that of a reference standard, which is generally set as a normal, healthy 30-year-old subject. The Z-Score is a comparison of a subject's bone mineral density to an age and sex matched standard.

"Degenerative bone disorder" refers to a disease or condition characterized by a decrease in bone mass and/or an increase in probability of fractures because of compromised structural integrity of the bone. Many degenerative bone disorders arise from an imbalance between bone formation and bone resorption. This imbalance can be caused by a reduction in osteoblast mediated bone formation, an increase in osteoclast mediated bone resorption, or a combination of changes to osteoblast and osteoclast activity. "Osteoblastogenesis" refers to the process of differentiation of stem cells and progenitor cells, such as mesenchymal stem cells, into functional osteoblasts. "Osteoclastogenesis" refers to the process of differentiation of stem cells and progenitor cells, such as monocyte/macrophage progenitor cells, into functional osteoclasts.

"Osteoporosis" refers to a degenerative bone disorder characterized by low bone mass and microarchitectural deterioration of bone tissue, leading to enhanced bone fragility and increased fracture risk. Primary osteoporosis represents bone mass loss unassociated with any other illness and is typically related to aging and age-related loss of gonadal function (e.g., postemenopausal osteoporosis and senile osteoporosis). Primary osteoporosis also includes idiopathic osteoporosis, which is osteoporosis where an underlying or secondary cause of the bone degeneration is unknown. Secondary osteoporosis refers to osteoporosis resulting from another condition or illness besides the age-related bone degeneration encompassed by primary osteoporosis. The WHO defines osteoporosis as bone density 2.5 standard deviations below the bone density of a reference standard (i.e., generally a healthy young adult of about 30 years old). In idiopathic osteoporosis affecting children and adults, there is no identifiable cause for the bone loss, including without limitation, the following diseases and conditions: hyper-calciuria, cystic fibrosis, thyrotoxicosis, celiac, Crohn's disease, ulcerative colitis, Rickets, osteomalacia, renal osteodystrophy, Paget's disease of the bone, osteogenesis imperfecta (OI), osteosarcoma, Ewing's sarcoma, multiple myeloma, metastatic breast and prostate cancer, oral bone loss, osteopenia, rheumatoid arthritis (RA), osteoarthritis (OA), or combinations thereof.

"Osteopenia" refers to a decrease in bone mineral density that is not as severe as osteoporosis, whether or not osteoporosis is present, as detected by a suitable diagnostic procedure, such as a radiographic technique. The WHO defines osteopenia as a bone density between 1 standard deviation and 2.5 standard deviations below the bone density of a reference standard as above Tumors can affect bone remodeling by various mechanisms, including, among others, releasing factors that affect osteoclast or osteoblast activity, crowding and destroying cells involved in bone metabolism, effects on hormone secretion (e.g., estrogen and parathyroid hormones), and adverse effects on organs involved in calcium metabolism. Exemplary tumors known to have a high predilection for metastasizing to bone are breast, prostrate, lung, and kidney cancers. For example, breast cancer can accelerate bone resorption by producing factors that stimulate osteoclast development, such as IL-1, IL-6, TGF-α, and tumor necrosis factor (TNF). Breast cancer cells are also known to produce parathyroid hormone-like protein (PTHrP), which binds PTH receptor and induces hypercalcemia, activates osteoclast activity, and increases renal absorption of calcium and excretion of phosphate.

Hematopoietic neoplasms, such as myeloid and lymphoid neoplasms, can also affect bone integrity by producing factors that regulate osteoclast and osteoblast development, destroying osteoclasts and osteoblasts in the bone marrow, and by differentiating into cells involved in bone remodeling. For example, in multiple myeloma, myeloma cells secrete TNF-α, TNF-β, RANKL, IL-1, and IL-6, all of which are known to affect osteoclast development and bone resorption. As an indication of this effect, osteoclasts can be found near the myeloid tumor cells, but not in parts of the bone where the myeloid tumor cells are absent.

Conversely, bone degeneration abnormalities can occur in subjects with decreased secretion or activity of PTH, namely hypoparathyroidism. This condition is found less frequently than hyperparathyroidism and can be caused by congenital disorders (e.g., parathyroid aplasia, DiGeorge syndrome, etc.), iatrogenic causes (e.g., removal of the parathyroid glands during thyroid or parathyroid surgery, radiation, etc.), and infiltration of the parathyroid glands (e.g., metastatic carcinoma, Wilson's disease, sarcoidosis, etc.). Hypoparathyroidism can also result from secretion of inactive forms of PTH or from attenuated response to PTH by bones and kidneys, but these conditions are generally rare occurrences. At the physiological level, low PTH activity can cause hypocalcemia and hyperphosphatemia.

In Paget's disease (osteitis deformans), commonly affected bones are the pelvis, collarbone, spine, skull, lower leg, thigh bones, and the humerus, excessive bone remodeling is found in localized regions. The initial stage of the disorder is characterized by increased bone resorption in a focal region, with an osteolytic lesion being a commonly detected abnormality upon radiological examination. The osteoclasts are larger than normal adult osteoclasts and show a higher number of nuclei. The excessive bone resorption is followed by an increase in bone formation, a stage characterized by increased number of normal appearing osteoblasts. The rapidly deposited bone, however, is structurally disorganized in appearance, being soft and porous in character, which accounts for the skeletal deformations and increased fracture risk. Reflecting the increased rate of bone remodeling, there are elevated levels of serum alkaline phosphatase and urinary excretions of hydroxyproline and pyridinoline.

Periodontal disease is believed to arise from an opportunistic infection by indigenous plaque forming bacteria followed by a time-dependent immune response that includes the remodeling of the subjacent connective tissues and bone. Although the exact disease mechanism is unknown, bacterial factors may act to induce host immune cells to release extracellular factors capable of stimulating osteoclastogenesis and/or inducing osteoblasts to release factors involved in recruitment and activation of osteoclasts. Various endotoxins may also inhibit bone formation by inhibiting osteoblastic collagen synthesis and by preventing development of osteoblasts. The end result is an imbalance between bone resorption and bone formation and a corresponding degeneration of the bone supporting the teeth. However, by regulating osteoclast activity, the rate of resorption of bone may be controlled, thereby preventing the complications associated with periodontal disease.

It is to be understood that the use of the regulators and inhibitors described herein are not limited to the degenerative bone disorders described herein, but may be applied to any degenerative bone disorder characterized by a net excess of bone formation over bone resorption. This condition may arise from decreased osteoclastogenesis or osteoclast activation, increased osteoblastogenesis or osteoblast activity, or combinations thereof. Thus, the methods herein encompass treatments for degenerative bone disorders in which there is generally an imbalance between bone resorption and bone formation.

The compounds referred to can be of any type, including in one embodiment, nucleic acid, polypeptide or other organic molecules. The present invention extends in various aspects to a pharmaceutical composition, medicament, drug or other composition comprising such a compound, a method comprising administration of such a composition, a method comprising administration of such a composition to a patient, e.g., for treatment of bone remodeling and bone formation disorders and pathologies, use of such a compound in the manufacture of a composition for administration, and a method of making a pharmaceutical composition comprising admixing such a compound with a pharmaceutically acceptable excipient, vehicle or carrier, and optionally other ingredients.

In one embodiment, provided herein is a method of enhancing bone formation in a subject, comprising the step of inhibiting, for example, LRRc17 expression in a subject, thereby decreasing or regulating osteoclast differentiation, enhancing anabolic activity of osteoblasts, increasing new bone formation, or combinations thereof. In one embodiment, inhibiting the expression or function of OB86, specifically LRRc17 is done by any of the embodiments or examples provided herein, and resulting in the inhibition of the differentiation or expression of osteoclasts.

To provide insight into what factors are regulated in osteoclasts upon exposure to stimulation factors, and which of those factors might be enriched or regulated in osteoclasts compared to other mesenchymal-derived cells, the present invention is further described by example. These exemplified embodiments are provided for purposes of illustration only, and are not intended to be limiting unless otherwise specified. The embodied scenarios are relevant for many practical situations, and are intended to be exemplary to those skilled in the art, but are not to be construed as limiting the scope of the invention or the appended claims.

mRNA expression profiles of osteoblasts. In brief, mRNA expression profiles were compared by PCR-select cDNA subtraction (using standard methods known in the art) between a fibroblast cell line and primary osteoblasts stimulated with Vit-D3. mRNA expression of selected genes was then examined in fibroblasts, osteoblasts and Vit-D3 stimulated osteoblasts (see FIG. 1). An "mRNA-coding region" of a gene consists of the nucleotide residues of the coding strand of the gene and the nucleotide residues of the non-coding strand of the gene which are homologous with or complementary to, respectively, an mRNA molecule which is produced by transcription of the gene. It is understood that, owing to mRNA processing which occurs in certain instances in eukaryotic cells, the mRNA-coding region of a gene may comprise a single region or a plurality of regions separated from one another in the gene as it occurs in the genome. Where the mRNA-coding region of a gene comprises separate regions in a genome, "mRNA-coding region" refers both individually and collectively to each of these regions.

In the exemplified embodiment, primary osteoblasts were obtained from calvarias of newborn C57BL/6 mice by conventional methods using collagenase as described previously (Kim et al., supra, 2002; Suda et al., *Methods Enzymol.* 282: 223-235 (1997)). Osteoblasts were cultured with Vit-D3 (for brevity, designated "OB/VU-D3") and used for preparation of a cDNA library. The OB/Vit-D3-enriched cDNA library was generated by using poly $A^+$ RNA from OB/Vit-DS and a fibroblastic cell line (NIH3T3) (Wong et al., supra, 1997; Kim et al., supra, 2002; Rho et al., *DNA Cell Biol.* 21:541-549 (2002)).

2 µg poly $A^+$ RNA from OB/Vit-D3 and NIH3T3 was used to make tester and driver cDNAs, respectively. Subtractive PCR was performed using the PCR-select cDNA subtraction kit according to the manufacturer's protocol (ClonTech Inc., Palo Alto, Calif.) (id). From the thus-created cDNA library, 171 clones were randomly selected and tested in the preliminary. Out of 171 clones tested, 85 clones showed higher expression in OB/Vit-D3 than NIH3T3, suggesting that −50% of the cDNA library contains OB/Vit-D3-enriched genes, which is as expected based on previous experience (id). The sequence analysis of the 85 clones revealed that they represented 42 independent genes, which were then grouped by patterns of mRNA expression following Northern analysis.

Figure 2:
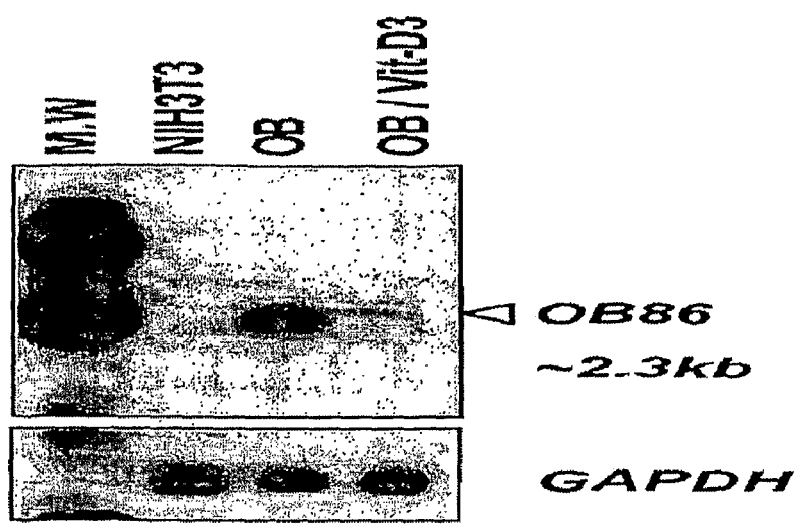
FIG. 2 is an image of a Northern blot showing the regulation of OB86 expression in primary osteoblasts.

For the Northern analyses, mRNAs were prepared from NIH3T3 cells, primary calvarial osteoblasts (OB) and primary calvarial osteoblasts stimulated with Vit-D3 ($5\times10^{-8}$ M) for 2 days. Among the 42 independent genes, 29 showed higher mRNA expression in osteoblasts than in NIH3T3, but demonstrated no further change in response to Vit-D3 stimulation. Eleven (11) genes showed higher mRNA expression in osteoblasts than in fibroblasts, and further up-regulation by Vit-D3 stimulation. Interestingly, the levels of mRNA of 2 of the genes expressed at a higher level in osteoblasts than in NIH3T3 cells, were significantly suppressed by Vit-D3 treatment. For example, mRNA expression of the clone OB86 in osteoblasts was much higher than was observed in NIH3T3 cells. Nevertheless, the expression levels were significantly reduced upon treatment with Vit-D3 (FIG. 2). Consequently, analyses were focused on clone OB86.

Figure 3:
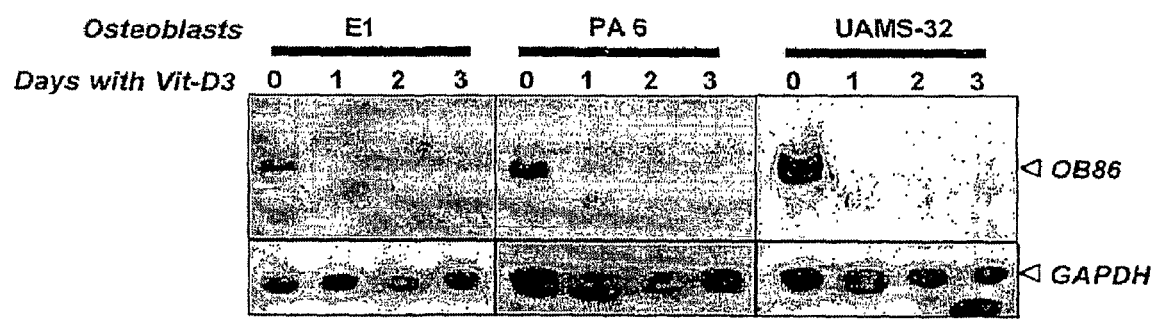
FIG. 3 is an image of Northern blot analyses showing the regulation of OB86 expression in osteoblastic cell lines E1, PA6 and UAMS-32.

To further characterize the regulation of OB86 expression in response to Vit-D3, three different osteoblastic cell lines (E1, PA6 (Takai et al., supra, 1998) and UAMS-32 (O'Brien et al., *J. Biol. Chem.* 274:19301-19308 (1999)) were used. These cell lines were treated with Vit-D3 ($5\times10^{-8}$ M) for three days and OB86 expression was determined (FIG. 3). As a result, as had been observed in primary calvarial osteoblasts, OB 86 expression was rapidly suppressed in the three different osteoblastic cell lines in response to Vit-D3.

Identification of LRRc17 as a Vit-D3 suppressed gene in osteoblasts. Upon sequence analysis, OB86 was shown to contain a partial cDNA fragment (the nucleotide 1961-2150 in the 3' untranslated region) of the gene called LRRc17, whose function was previously currently unreported. A putative LRR-containing protein, LRRc17, was originally identified as p37NB by subtraction cDNA analysis of genes expressed more abundantly in an S-type neuroblastoma cell line, as compared with a N-type neuroblastoma cell line (Kim et al., *Biochim. Biophys. Acta* 1309:183-188 (1996)). Subsequently it was characterized by a large scale mRNA analysis of human pancreas (Strausberg et al., *Proc. Natl. Acad. Sci. USA* 99:16899-16903 (2002)), and by the complete sequence analysis of human chromosome 7 (Hillier et al., *Nature* 424: 157-164 (2003)). The putative amino acid sequence analysis shows that LRRc17 is a secreted protein and contains 5 leucine rich repeats (at amino acids 106-129, 131-153, 269-293, 293-316, and 318-340), which are characterized by regions 22-28 amino acid residues in length, with consensus sequences of LxxLxLxxN/CxL (FIG. 4; SEQ ID No:1). To further study the role of LRRc17, a full-length LRRc17 cDNA was obtained by RT PCR using mRNA from primary calvarial osteoblasts of mouse and the sequence information in the NCBI database.

In one embodiment provided herein is an isolated nucleic acid molecule, degenerate variants thereof, fragments thereof, or analogs or derivatives thereof, which encodes LRRc17, conserved variants thereof, fragments thereof, or analogs or derivatives thereof. Examples of such isolated nucleic acid molecules comprise a DNA sequence encoding the amino acid sequence set forth in SEQ ID No:1, degenerate variants of these sequences, fragments thereof, or analogs or derivatives thereof. In other embodiments, these isolated nucleic acid molecules encode LRRc17 a full length, or naturally occurring forms of this enzyme subunit, and any antigenic fragments thereof from any animal; such as mammalian, or in another embodiment human, source. In one embodiment, due to degenerate nature of codons in the genetic code, LRRc17 can be encoded by numerous degenerate variants of isolated nucleic acid molecules provided herein. "Degenerate" refers in one embodiment to the use of different three-letter codons to specify a particular amino acid of the genetic code.

An "isolated nucleic acid" is considered to be "substantially pure" as used herein, and refers to a nucleic acid sequence, segment, or fragment which has been purified from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids. and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

In another embodiment, provided herein is vector comprising the isolated nucleic acid sequence encoding LRRc17 or any part of OB86, and may further comprise inhibitors thereof, such as Vit-D3. The term "vector" as used herein, refers to a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. Provided herein are cloning vectors comprising the isolated nucleic acid molecule of the present invention, or degenerate variants thereof, fragments thereof, analogs or derivatives thereof, and an origin of replication. In one embodiment, the term "origin of replication" refers to those DNA sequences that participate in DNA synthesis.

In one embodiment, provided herein is a vector comprising an isolated nucleic acid molecule comprising a sequence encoding SEQ ID NO:1, degenerate variants thereof, fragments thereof, or analogs or derivatives thereof, which encodes LRRc17 or any part of OB86, and may further comprise inhibitors thereof, such as Vit-D3, conserved variants thereof, fragments thereof, or analogs or derivatives thereof, and an origin of replication. In another embodiment, the vector as provided herein comprises an isolated nucleic acid molecule hybridizable under standard hybridization conditions to an isolated nucleic acid molecule comprising a sequence encoding SEQ ID NO:1, degenerate variants thereof, fragments thereof, or analogs or derivatives thereof, and an origin of replication. A large number of vector-host systems known in the art may be used. In one embodiment, the vectors are a plasmid, cosmid, yeast artificial chromosome (YAC), BAC, adenovirus, lentivirus, adeno-associated virus, retrovirus, P1, bacteriophage or eukaryotic viral DNA, so long as the vector system is compatible with the host cell used in certain embodiments. Examples of suitable vectors include bacteriophage T7-based expression vectors for replication and expression in bacteria, the pMSXND expression vector for replication and expression in mammalian cells and baculovirus-derived vectors for replication and expression in insect cells In other embodiments, vectors having applications in the present invention include, but are not limited to *E. coli* bacteriophages, such as lambda derivatives, or plasmids, such as pBR322 derivatives or pUC plasmid derivatives, e.g., pGEX-vectors, pmal-c, pFLAG, etc. The insertion an isolated nucleic acid molecule, as provided herein, to a cloning vector can, for example, be accomplished by ligating the isolated nucleic acid molecule into a vector which has complementary cohesive termini. In another embodiment, if the complementary restriction sites used to fragment the isolated nucleic acid, degenerate variants thereof, fragments thereof, or analogs or derivatives thereof, or an isolated nucleic acid hybridizable thereto under standard hybridization conditions, are not present in the vector, the ends of the isolated nucleic acid molecule, degenerate variants thereof, fragments thereof, or analogs or derivatives thereof, or an isolated nucleic acid molecule hybridizable thereto under standard hybridization conditions may be enzymatically modified. In one embodiment, any site desired may be produced by ligating nucleotide sequences (linkers) onto the DNA termini; these ligated linkers may comprise in other embodiments, specific chemically synthesized oligonucleotides encoding restriction endonuclease recognition sequences.

Such recombinant molecules are introduced in other embodiments into host cells via transformation, transfection, infection, electroporation, etc., so that many copies of an isolated nucleic acid molecule of the present invention, degenerate variants thereof, fragments thereof, or analogs or derivatives thereof can be generated. In one embodiment, cloned isolated nucleic acid molecule are contained on a shuttle vector plasmid, which provides for expansion in a cloning cell, e.g., *E. coli*, and facile purification for subsequent insertion into an appropriate expression cell line, if such is desired. For example, a shuttle vector, referring to a vector that can replicate in more than one type of organism, can be prepared for replication in both *E. coli* and *Saccharomyces cerevisiae* by linking sequences from an *E. coli* plasmid with sequences from the yeast plamid. In fact, LRRc17 has now been produced in *E. coli*.

In one embodiment, provided herein is a polypeptide, encoded by the nucleic acid for LRRc17 or by a portion of OB86, as set forth in SEQ ID NO:1, degenerate variants thereof, fragments thereof, or analogs or derivatives thereof, conserved variants thereof, and an origin of replication. In another embodiment the invention comprises the amino acid sequence having the sequence as set forth in SEQ ID No:1, and may further comprise inhibitors thereof, such as Vit-D3. "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. Conventional notation is used herein to portray polypeptide sequences: the left-hand end of a polypeptide sequence is the amino-terminus; the right-hand end of a polypeptide sequence is the carboxyl-terminus.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego). As used herein, an "essentially pure" preparation of a particular protein is a preparation wherein at least about 95%, and preferably at least about 99%, by weight, of the protein in the preparation is the particular protein. The term "substantially pure" describes a compound, e.g., a protein or polypeptide which has been separated from components which naturally accompany it. Typically, a compound is substantially pure when at least 10%, at least 20%, at least 50%, at least 60%, at least 75%, at least 90%, or at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

In another embodiment, the term "polypeptide," when in reference to any peptide of this invention, is meant to include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells, such as an osteoclast cell in certain embodiments. Such modifications include, but are not limited to N-terminal, C-terminal or peptide bond modifications, including, but not limited to, backbone modifications, and residue modification, each of which represents an additional embodiment of the invention. Methods for preparing peptidomimetic compounds are well known in the art and are specified, for example, in *Quantitative Drug Design*, Ramsden, ed., Chapter 17.2, F. Choplin Pergamon Press (1992).

In one embodiment, the term "antibody" include complete antibodies (e.g., bivalent IgG, pentavalent IgM) or fragments of antibodies in other embodiments, which contain an antigen binding site. Such fragment include in one embodiment Fab, $F(ab')_2$, Fv and single chain Fv (scFv) fragments. Such fragments may or may not include antibody constant domains. The invention includes antibodies and antibody fragments which are produced in bacteria and in mammalian cell culture. An antibody obtained from a bacteriophage library can be a complete antibody or an antibody fragment. Complete antibodies may be obtained from such a library by replacing missing constant domains once a desired $V_H$-$V_L$ combination has been identified.

The antibodies described herein can be monoclonal antibodies (Mab) or polyclonal antibodies. Antibodies of the invention which are useful for the compositions and methods described herein can be from any source, and in addition may be chimeric. In one embodiment, sources of antibodies can be from a mammal, including a mouse, rat, etc, or from a human. Antibodies of the present invention which are useful have reduced antigenicity in humans, or are non-antigenic in humans. Chimeric antibodies may be used herein, containing human amino acid sequences and include humanized antibodies which are non-human antibodies substituted with sequences of human origin to reduce or eliminate immunogenicity, but which retain the binding characteristics of the non-human antibody. In one embodiment, the antibody used to modulate function of LRRc17 or a portion of OB86, including a LRRc17- or OB86-specific monoclonal antibody (MoAb).

In certain embodiments, the antibodies employed in the compositions described herein and used in the methods described herein, will be "humanized," part-human or human antibodies. In one embodiment, "humanized" antibodies are chimeric monoclonal antibodies from mouse, rat, or other non-human species, bearing human constant and/or variable region domains ("part-human chimeric antibodies"). Various humanized monoclonal antibodies for use in the present invention will be chimeric antibodies wherein at least a first antigen binding region, or complementarity determining region (CDR), of a mouse, rat or other non-human monoclonal antibody is operatively attached to, or "grafted" onto, a human antibody constant region or "framework." "Humanized" monoclonal antibodies for use herein may also be monoclonal antibodies from non-human species wherein one or more selected amino acids have been exchanged for amino acids more commonly observed in human antibodies. This can be readily achieved through the use of routine recombinant technology, particularly site-specific mutagenesis.

In one embodiment, the isolated nucleic acids used in the compositions and methods described herein have a nucleic acid sequence of about 65% to about 99% similarity with the nucleic acid encoding the amino acid sequence of SEQ ID No:1, including variants and fragments thereof. In another embodiment, the oligonucleotide has a base sequence containing an at least 15 contiguous base region that is at least 70% complementary, at least 80% complementary, at least 90% complementary, or 100% complementary to an-at least 15 contiguous base region present on a reference gene sequence (excluding RNA and DNA equivalents) encoding LRRc17 or a portion of OB86. (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity can also be expressed in terms of the number of base mismatches present in each set of at least 15 contiguous bases being compared, which may range from 0-3 base mismatches, so long as their functionality for the purpose used is not compromised.

In another embodiment, the gene encoding the LRRc17 or portion of OB86 protein as described herein, refers to the sequence being sufficiently complimentary to its reference sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic nucleotides), but in which the entire complementary base sequence is capable of specifically hybridizing with another base sequence under appropriate hybridization conditions. Contiguous bases are at least about 80%, 90% or 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., see Sambrook et al., *Molecular Cloning. A Laboratory Manual,* 2nd ed. (Cold Spring Harbor Laboratory Press, Cold Spring Harbor, N.Y., 1989).

It will be appreciated by those skilled in the art that DNA sequence polymorphisms that lead to changes in the amino acid sequences of LRRc17 may exist within a population (e.g., the mouse or human population). Such genetic polymorphism in the gene encoding LRRc17 or portions thereof may exist among individuals within a population due to natural allelic variation. An allele is one of a group of genes which occur alternatively at a given genetic locus. Such natural allelic variations can typically result in 1-5% variance in the nucleotide sequence of the gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms in LRRc17 or portions thereof that are the result of natural allelic variation and that do not alter the functional activity of LRRc17, or its inhibitors, such as Vit-D3, are intended to be within the scope of the invention.

Moreover, nucleic acid molecules encoding LRRc17 or portions thereof from other species (LRRc17 homologues), which have a nucleotide sequence which differs from that of a human LRRc17, are intended to be within the scope of the invention. Nucleic acid molecules corresponding to natural allelic variants and homologues of the LRRc17 cDNA of the invention can be isolated based on their identity to the human LRRc17 nucleic acids encoding the LRRc17 amino acid disclosed herein using the human cDNAs, or a portion thereof, as a hybridization probe according to standard hybridization techniques under stringent hybridization conditions. For example, splice variants of human and mouse LRRc17 cDNA can he isolated based on identity to human and mouse LRRc17.

In one embodiment, provided herein is a LRRc17 polypeptide, having an amino acid sequence having at least 60% similarity with the amino acid sequence of SEQ ID No:1. In another embodiment the peptide has a amino acid sequence having at least 65%, or 75%, or 85%, or 95% similarity with the amino acid sequence of SEQ ID No:1, including in other embodiments, variants and fragments thereof as describe herein. In one embodiment, provided herein is a method for detecting osteoclast specific LRRc17 expressing cells in a mixed cells population, comprising: identifying cells expressing SEQ ID No:1, including variants, fragments and mutants, thereof whereby expression of such sequences indicate a LRRc17 osteoclast cell.

Tissue distribution of LRRc17 mRNA. In an examination of mRNA expression patterns of LRRc17 among various tissues in adult mice (FIG. 5), the level of LRRc17 mRNA was shown to be considerably higher in osteoblasts than in any other examined tissue. Other than in bone, significant levels of LRRc17 mRNA was detected in heart and lung, indicating that LRRc17 plays a primary role in bone metabolism.

Mice are used throughout the discussions herein, and may include transgenic animal models because they are easy to house, relatively inexpensive, and easy to breed. However, other non-human transgenic mammals may also be made in accordance with the present invention and in certain embodiments, such as monkeys, sheep, rabbits or rats. In one embodiment, transgenic animals refer to those animals that carry a transgene, which is a cloned gene introduced and stably incorporated, which is passed on in another embodiment, to successive generations. In an embodiment of the present invention, the LRRc17 gene was cloned and stably incorporated into the genome of a mouse. Alternatively, altered portions of the LRRc17 gene sequences may be used in other embodiments. In this manner, the specific function of alternatively spliced gene products may be investigated during animal development and initiation of disease states in order to develop therapeutic strategies or to identify biologically active agents to be used in the methods described herein, or in the compositions described herein.

Regulation of LRRc17 expression by Vit-D3 and its relationship to TRANCE or OPG expression in osteoblasts. Pro-osteoclastogenic factors generally up-regulate expression of TRANCE, while suppressing OPG expression, with the converse being true for anti-osteoclastogenic factors. The degree of regulation varies depending on the culture conditions and cells used. Therefore, the expression of LRRc17 was compared with that of TRANCE in response to Vit-D3 in osteoblastic cell line, UAMS-32. For this comparison, cells were treated with Vit-D3 ($5 \times 10^{-8}$ M) for 3 days, after which LRRc17 mRNA expression was determined. As noted above, Vit-D3 treatment rapidly up-regulated the expression of TRANCE in UAMS-32 cells. Interestingly, expression of LRRc17 was almost completely suppressed by a one day treatment with Vit-D3 (FIG. 6A).

Similar experiments were carried out with primary calvarial osteoblasts (FIG. 6B). Vit-D3 treatment rapidly induced TRANCE mRNA, while suppressing OPG mRNA. After 3 days, the level of OPG was slightly increased, while TRANCE mRNA expression level reached the baseline, indicating bi-phasic control of TRANCE/OPG expression by Vit-D3. In primary osteoblasts, the regulation of LRRc17 by Vit-D3 is also bi-phasic, mirroring that of OPG expression (FIG. 6B). Thus, the change in the expression pattern of LRRc17 in response to Vit-D3 positively correlates with that of OPG, but inversely correlates with TRANCE expression (FIG. 6).

LRRc17 inhibition of osteoclastogenesis. Because LRR motifs are found in a variety of cytoplasmic, membrane and extracellular proteins, and are associated with widely varied functions, a common property of an LRR is involvement in protein-protein interactions. In addition, data showing that osteoblastic LRRc17 expression directly correlates with OPG, and inversely correlates with TRANCE in response to Vit-D3, indicates participation of LRRc17 in the cell-cell communication between osteoblasts and osteoclasts, leading to examination of LRRc17 regulation of osteoclast differentiation.

To test the role of LRRc17 regulation in osteoclast differentiation, LRRc17 was transfected into osteoblastic cell line, UAMS-32. To overcome the suppressive effect of Vit-D3, the LRRc17 was introduced under the control of an oncogenic murine sarcoma virus (MSV) long terminal repeat (LTR) promoter. MSV LTR when operably linked to the coding region of a gene, is able to promote transcription of the coding region. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region. Mouse fibroblasts transformed by MSV are highly sensitive to the antiproliferative effect of certain compositions.

"Transfection" refers to a cell that has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element, such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A "clone" is a population of cells derived from a single cell or ancestor by mitosis. A "cell line" is a clone of a primary or other cell that is capable of stable growth in vitro for many generations. An organism, such as a plant or animal, which has been transformed with exogenous DNA is termed "transgenic," such as a transgenic mouse.

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well. A host cell that comprises a recombinant polynucleotide is referred to as a "recombinant host cell." A gene which is expressed in a recombinant host cell wherein the gene comprises a recombinant polynucleotide, produces a "recombinant polypeptide."

As used herein, the term "promoter" or "promoter/regulatory sequence" means a nucleic acid sequence which is required for expression of a gene product operably linked to the promoter/regulator sequence. In some instances, this sequence may be the core promoter sequence, while in other instances this sequence may also include an enhancer sequence and other regulatory elements which are required for expression of the gene product. The promoter or promoter/regulatory sequence may, for example, be one which expresses the gene product in a tissue specific manner. A "constitutive promoter" is a promoter which drives expression of a gene to which it is operably linked, in a constant manner in a cell. By way of example, promoters which drive expression of cellular housekeeping genes are considered to be constitutive promoters. An "inducible" promoter is a nucleotide sequence which, when operably linked with a polynucleotide which encodes or specifies a gene product, causes the gene product to be produced in a living cell substantially only when an inducer which corresponds to the promoter is present in the cell.

Wild-type LRRc17 cDNA containing the open-reading frame was subcloned into bicistronic retroviral vector pMX-IRES-EGFP to yield pMX-LRRc17-IRES-EGFP according to the methods described by (Morita et al., *Gene Ther.* 7:1063-1066 (2000); Kadono et al., *EMBO Rep.* 6:171-176 (2005), both of which are herein incorporated by reference). Enhanced Green Fluorescence Proteins (EGFP) are expressed and purified from transformed cells using recognized methods that ensure high purity and maximal GFP fluorescence. Recombinant EGFP is a 29 kDa monomer with 265 amino acids, which acts as recognized control reagents for expression studies and can also be conjugated to other proteins. The gene is inserted upstream of the IRES (internal ribosomal entry site) sequence so that both LRRc17 and EGFP are expressed from a single messenger RNA (mRNA) in the same cells. Cells may be sorted based on EGFP expression, e.g., by FACSVantage (Becton Dickinson, San Jose, Calif.), and expanded in growth medium.

UAMS-32 was co-transfected with pMX-LRRc17-IRE-SEGFP and pMX-Puro (at the ratio of 20:1) and selected with puromycin (3 μg/ml). In one embodiment, flow cytometric analysis is carried out to quantify morphologic changes and to confirm the expression of EGFP in the transfectants on, e.g., a FACSCalibur flow cytometer (Becton Dickinson).

Puromycin-resistant clones were tested for EGFP expression by fluorescent microscopy. To examine the function of LRRc17 during osteoclastogenesis, 4 clones (puromycin-resistant and EGFP-positive) were randomly selected, and their respective abilities to support osteoclast differentiation were evaluated in the presence of Vit-D3. UAMS-32 transfectants ($1 \times 10^4$ cells) and bone marrow cells ($1 \times 10^5$ cells) were co-cultured in the presence or absence of $10^{-8}$ M Vit-D3 in 0.2 ml minimum essential (alpha) medium (αMEM) containing 10% FBS (fetal bovine serum) in 96-well culture plates. After 6 days of culture, cells were fixed and stained for tartrate-resistant acid phosphatase (TRAP) as described (Yasuda et al., supra, 1998a and 1998b, both of which are herein incorporated by reference).

The cells were then counted and TRAP-positive multinucleated cells were counted as osteoclast-like multinucleated cells (MNCs). Similar to the parental cell line, UAMS-32 cells, when transfected with control pMX-IRES-EGFP, induced differentiation of bone marrow cells into TRAP(+) multinucleated osteoclasts in response to Vit-D3. However, when LRRc17 was constitutively expressed in UAMS-32 cells, Vit-D3-induced osteoclast differentiation was significantly reduced (FIG. 7). When combined, these results demonstrate that suppression of LRRc17 by Vit-D3 is critical for osteoclast differentiation induced by Vit-D3-activated osteoblasts, and identify LRRc17 as an osteoblast-produced inhibitor of osteoclastogenesis.

Given that LRRc17 acts as a soluble (secreted) inhibitory factor as predicted by amino acid sequence analysis, the ability of LRRc17 was examined to confirm that it could inhibit the differentiation of osteoclasts, in general, as well as when induced by activated osteoblasts. Thus, bone marrow-derived macrophages were transduced with retroviruses expressing LRRc17 (pMX-LRRc17-IRES-GFP) or control retroviruses (pMX-IRES-GFP) as above (Kadono et al., supra, 2005). In brief, bone marrow cells were obtained by flushing femurs and tibiae from 6-8 week-old mice. Bone marrow cells were cultured in αMEM containing 10% FBS with M-CSF (30 ng/ml) as above for 2 days. Floating cells were removed and attached bone marrow-derived monocyte cells (BMM cells) were used for retroviral transduction. To generate the viral stocks, retrovirus packaging cell line Plat-E cells (Morita et al., Gene Ther. 7:1063-1066 (2000)) were transfected with pMX-LRRc17-IRES-EGFP or with the control vector pMX-IRES-EGFP. Viral supernatant was collected from cultured media 36 hours after transfection.

Figure 8:
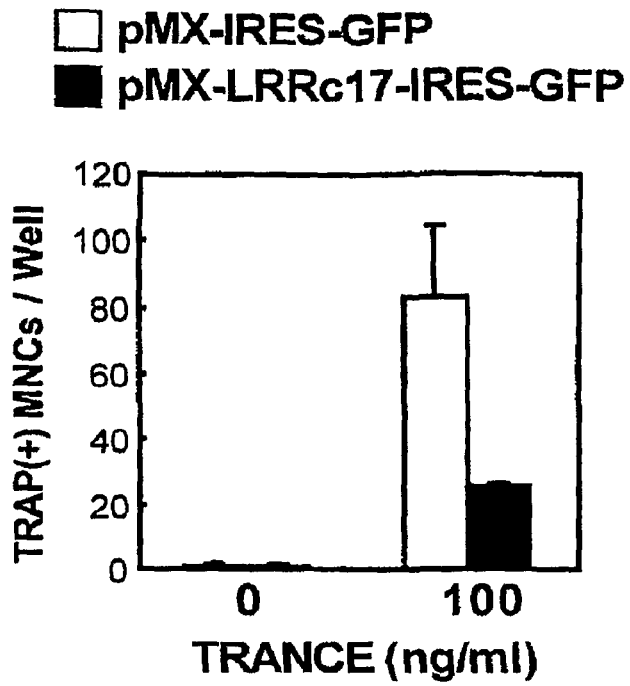
FIG. 8 is a graph showing that LRRc17 expression inhibits osteoclast differentiation from bone marrow precursors stimulated with M-CSF and TRANCE.

BMM cells were then incubated with the virus supernatant for 8 hours in the presence of polybrene (10 μg/ml). Polybrene is a charged cationic polymer used to increase the efficiency of infection (transduction) of certain cells with a retrovirus in cell culture. After removing the virus supernatant, BMMs were harvested and further cultured in the presence of M-CSF by the Kadono method above. The EGFP-expressing BMMs were subsequently purified and stimulated with M-CSF (30 ng/ml) in the absence or presence of TRANCE (100 ng/ml) in 96-well culture plates ($3 \times 10^4$/0.2 ml/well). After 3 days, cells were fixed and stained for TRAP. Multinucleated TRAP(+) cells were counted as osteoclasts. Consistent with the finding that LRRc17 functions as an inhibitor of osteoclast differentiation in general, the number of TRAP(+) osteoclast-like multinucleated cells was significantly reduced when BMMs expressing LRRc17 were used as osteoclast precursors, as compared to when BMMs expressing control EGFP only (FIG. 8).

Although it was not possible to directly determine the actual level of LRRc17 in the culture by only the co-culture experiments (FIG. 8) and the expression of surrogate markers (EGFP), these results did further confirm that LRRc17 functions as an inhibitory molecule for osteoclastogenesis. In addition, the regulation of LRRc17 expression in osteoblasts by Vit-D3 further demonstrates that LRRc17 is an osteoblast-produced factor that mediates the communication between osteoblasts and osteoclasts, and is critical for ensuring proper regulation of osteoclast differentiation in response to various osteotropic factors.

Thus, in one embodiment, provided herein is a method for controlling osteoclast differentiation and for identifying a modulator of osteoclast differentiation comprising: contacting the cell with a candidate agent; and analyzing said agent for its ability to modulate osteoclast differentiation, genes regulated by the expression of SEQ ID No:1, or activity of a polypeptide encoded thereby, whereby an ability of the candidate agent to down-regulate or up-regulate the osteoclast differentiation, genes regulated by the expression of SEQ ID No:1, or its encoded polypeptides indicate the agent is a modulator. "Contacting" a cell with a substance refers to (a) providing the substance to the environment of the cell (e.g., solution, in vitro culture medium, anatomic fluid or tissue); or (b) applying or providing the substance directly to the surface of the cell, in either case so that the substance comes in contact with the surface of the cell in a manner allowing for biological interactions between the cell and the substance, which in another embodiment, is the candidate agent. It is to be understood that the use of the term "modulates" refers herein to stimulating, enhancing, inhibiting or abrogating, as defined herein. Modulating osteoclast differentiation refers to LRRc17 expression and/or activity via LRRc17 ubiquitination and/or degradation.

In one embodiment, the agent identified using the methods described herein is a composition for use in modulating osteoclast differentiation comprising LRRc17 or OB86. In one embodiment, provided herein is a method for treatment of a disease linked to osteoclast differentiation, comprising the step of administering to a patient suffering from such a disease the compositions described herein. In one embodiment, provided herein is a method of decreasing bone mass in a subject, comprising the step of administering to the subject an agent able to modulate the expression or function of a gene controlling osteoclast differentiation in the subject, thereby enhancing bone resorption, reducing bone formation, or a combination thereof.

Pharmaceutical Compositions and Administration. The active compound(s), or compositions thereof, will generally be used in an amount effective to treat or prevent the particular disease being treated (a "therapeutic amount"). The compound(s) can be administered therapeutically to achieve therapeutic benefit or prophylactically to achieve prophylactic benefit. By "therapeutic benefit" is meant eradication or amelioration of the underlying degenerative bone disorder being treated and/or eradication or amelioration of one or more of the symptoms associated with the underlying disorder such that the patient reports an improvement in condition, notwithstanding that the patient may still be afflicted with the underlying disorder. Therapeutic benefit also includes halting or slowing the progression of the disease, regardless of whether improvement is realized. For prophylactic administration, the active compound can be administered to a patient at risk of developing a disorder characterized by, caused by or associated with bone loss and/or compromised bone integrity.

In one embodiment, provided herein is a method of inhibiting bone resorption in a subject, comprising administering to said subject and agent capable of inhibiting the expression or function of a gene encoding at least a portion of OB86, specifically LRRc17, thereby inhibiting osteoclast cell-to-cell fusion or osteoclast maturation. As used herein, the term "bone resorption" refers to the undesired loss of bone caused at least in part by osteoclast activity. In another embodiment, the term "inhibit" refers to a decrease in the amount, quality, or effect of a particular activity, and it is used interchangeably with the terms "reduce," "minimize," and "lessen" and refers to, in other embodiments, the reduction of expression or function of at least a portion of OB86, specifically LRRc17 by the administration of a therapeutically effective amount of the agents and compositions described herein to a patient, using the methods described herein.

The term "treatment," or "treating" refers to any process, action, application, therapy, or the like, wherein a subject, including a human being, is subjected to medical aid with the object of improving the subject's condition, directly or indirectly. The term "treating" refers also to reducing incidence, or alleviating symptoms, eliminating recurrence, preventing recurrence, preventing incidence, improving symptoms, improving prognosis or combination thereof in other embodiments. "Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent pathology. The alleviation of a condition that results in a more serious condition is encompassed by this term. Therefore, in one embodiment, provided herein a method of treating a pathology, such as osteoporosis in another embodiment; associated with increased bone resorption, decreased bone formation or a combination thereof, in a human subject, administering to said subject an effective amount of a composition comprising an agent able to inhibit the expression or function of a gene encoding a portion of OB86 or LCCRc17 in the subject, thereby inhibiting bone resorption, increasing bone formation or a combination thereof and treating a pathology associated with increased bone resorption, decreased bone formation or a combination thereof.

In one embodiment, the term "therapeutically effective amount" refers to an amount of a compound which produces a medicinal effect observed as reduction in the rate of bone loss in an individual, or in another embodiment, increase in bone formation (both as measured in density or rate) when a therapeutically effective amount of an agent or compositions as described herein, is administered to an individual who is susceptible to, or suffering from, a disease characterized by bone loss. Therapeutically effective amounts are typically determined by the effect they have compared to the effect observed when a composition which includes no active ingredient (i.e., a control) is administered to a similarly situated individual. In another embodiment, the term "diseases characterized by bone loss" refers to diseases, conditions, disorders and syndromes which have as a symptom or pathology a decrease in bone mass or density. Such diseases, without intended limitation, include osteoporosis, osteopenia, rickets, osteomalacia, renal osteodystrophy, Paget's disease of the bone, osteogenesis imperfecta (OI), osteosarcoma, Ewing's sarcoma, multiple myeloma, metastatic breast and prostate cancer, oral bone loss, osteopenia, rheumatoid arthritis (RA), osteoarthritis (OA), or combinations thereof.

The amount of inhibitor compound(s) administered will depend upon a variety of factors, including, for example, the particular indication being treated, the mode of administration, whether the desired benefit is prophylactic o therapeutic, the severity of the indication being treated and the age and weight of the patient, the bioavailability of the particular active compound, etc. Determination of an effective dosage is well within the capabilities of those skilled in the art.

Initial dosages can be estimated initially from in vitro assays. For example, an initial dosage for use in animals can be formulated to achieve a circulating blood or serum concentration of compound that sufficiently inhibits LRRc17 to inhibit osteoclast activity in a dentin pit assay. Alternatively, an initial dosage for use in animals can be formulated to achieve a circulating blood or serum concentration of active compound that is equal to or greater than the $IC_{50}$ as measured in an inhibition assay. Calculating dosages to achieve such circulating blood or serum concentrations taking into account the bioavailability of the particular inhibitor compound is well within the capabilities of skilled artisans. For guidance, see, Fingl and Woodbury, "General Principles," In: *The Pharmaceutical Basis of Therapeutics*, Chapter 1, pp. 1-46, 1975, and the references cited therein.

Initial dosages can also be estimated from in vivo data, such as in animal models. Dosage amounts will typically be in the range of from about 1 mg/kg/day to about 100 mg/kg/day, 200 mg/kg/day, 300 mg/kg/day, 400 mg/kg/day or 500 mg/kg/day, but can be higher or lower, depending upon, among other factors, the activity of the inhibitory compound, its bioavailability, the mode of administration and various factors discussed above. Dosage amount and interval can be adjusted individually to provide plasma levels of the active compound(s) which are sufficient to maintain therapeutic or prophylactic effect. In cases of local administration or selective uptake, such as local topical administration, the effective local concentration of active compound(s) can not be related to plasma concentration. Skilled artisans will be able to optimize effective dosages without undue experimentation.

The compound(s) can be administered once per day, a few or several times per day, or even multiple times per day, depending upon, among other things, the indication being treated and the judgment of the prescribing physician. Preferably, the active compound(s) will provide therapeutic or prophylactic benefit without causing substantial toxicity. Toxicity of the active compound(s) can be determined using standard pharmaceutical procedures. The dose ratio between toxic and therapeutic (or prophylactic) effect is the therapeutic index. Active compound(s) that exhibit high therapeutic indices are preferred.

The desired dosage of active compound in the compositions described herein, which may be used for the methods described herein will vary, depending on the mode of administration, the condition to be treated, the overall condition of the subject, and the compound administered. It is anticipated that in one non-limiting embodiment, where the systemic administration of the compositions described herein by injection is desired, the appropriate dosage will be between 1 mg to 20 mg of the agent able to inhibit the expression or function of a gene LRRc17 or OB86 in the subject per kg body weight.

Depending on the subject and the condition to be treated, in one embodiment, dosages will be between about 1 to about 10 mg per kg body weight for subjects whose existing bone density is not extremely low; or, in another embodiment, between about 10 mg to about 20 mg per kg body weight for subjects whose bone density is extremely low.

Where localized administration of the compositions described herein is desired, the appropriate localized dosage can be determined with reference to the level of compound desired in the treatment area. In another embodiment, the total dosage required for localized treatment will be lower than that level required for systemic treatment, and in one embodiment, the appropriate localized dosage will be ten to one-hundred fold lower than the amount of compound required for systemic treatment.

When used to treat degenerative bone disorders or prevent bone loss, OB86 or the LRRc17 inhibitor compounds can be administered singly, as mixtures of one or more active compounds or as a mixture or combination with other agents useful for treating such diseases and/or symptoms associated with such diseases. The active compounds can be administered per se or as pharmaceutical compositions. Pharmaceutical compositions comprising the active compounds of the invention can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries that facilitate processing of the active compounds into preparations which can be used pharmaceutically. The actual pharmaceutical composition administered will depend upon the mode of administration. Virtually any mode of administration can be used, including, for example, topical, oral, systemic, inhalation, injection, transdermal, etc The active compound can be formulated in the pharmaceutical compositions per se, or in the form of a pharmaceutically acceptable salt. As used herein, the expression "pharmaceutically acceptable salt" means those salts which retain substantially the biological effectiveness and properties of the active compound and which is not biologically or otherwise undesirable. Such salts can be prepared from inorganic and organic acids and bases, as is well-known in the art. Typically, such salts are more soluble in aqueous solutions than the corresponding free acids and bases.

For topical administration, the active compound(s) can be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal, oral, or pulmonary administration. Useful injectable preparations include sterile suspensions, solutions or emulsions of the active compound(s) in aqueous or oily vehicles. The compositions can also contain formulating agents, such as suspending, stabilizing and/or dispersing agent. The formulations for injection can be presented in unit dosage form, e.g., in ampules or in multidose containers, and can contain added preservatives.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings. Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration can be suitably formulated to give controlled release of the active compound.

Other methods of administration, e.g., buccal, rectal, vaginal, transmuscosal or by aerosol are also contemplated herein by recognized means. Alternatively, transdermal delivery systems can be used or manufactured as an adhesive disc or patch which slowly releases the active compound(s) for percutaneous absorption. Suitable transdermal patches are described in for example, U.S. Pat. Nos. 5,407,713; 5,352,456; 5,332,213; and the like. For prolonged delivery, the active compound(s) can be formulated as a depot preparation, for administration by implantation; e.g., subcutaneous, intradermal, or intramuscular injection. Thus, for example, the active ingredient can be formulated with suitable polymeric or hydrophobic materials (e.g., as an emulsion in an acceptable oil) or ion exchange resins, or as sparingly soluble derivatives; e.g., as a sparingly soluble salt. Additionally, other pharmaceutical delivery systems can be employed. Liposomes and emulsions are well-known examples of delivery vehicles that can be used to deliver active compounds(s). Certain organic solvents, such as dimethylsulfoxide (DMSO) can also be employed, although usually at the cost of greater toxicity.

The pharmaceutical compositions can, if desired, be presented in a pack, kit or dispenser device which can contain one or more unit dosage forms containing the active compound(s). The pack or kit can, for example, comprise metal or plastic foil, such as a blister pack. The pack, kit or dispenser device can be accompanied by instructions for administration.

In one embodiment, the agent used in the compositions and methods described herein, affects the maturation or function of osteoclasts in the subject. In another embodiment, osteoclasts treated with the compositions and agents described herein are smaller than wild-type osteoclasts, which are usually >100 μm in diameter. The formation of large (>100 μm) osteoclasts containing more than 5 nuclei and an actin ring will greatly diminish in the presence of agents capable of inhibiting the expression or function of LRRc17.

In one embodiment, the agent used in the compositions and methods described herein, is a siRNA, a miRNA, a virus, polyamides, triple-helix-forming agents, antisense RNA, synthetic peptide nucleic acids (PNAs), agRNA, LNA/DNA copolymers, or a combination thereof, specifically against the gene encoding LRRc17.

To further characterize the role of LRRc17 in osteoclast differentiation, the following Examples are provided.

EXAMPLES

Example 1

Regutation of LRRc17 expression in osteoblasts in response to osteotropic factors. Since the discovery of the TRANCE-RANK-OPG axis, numerous studies have shown that most osteotropic factors regulate osteoclast differentiation by modulating the ratio of TRANCE versus OPG expressed by osteoblasts. TRANCE and OPG expression is often, though not always, inversely regulated by osteotropic factors. More importantly, pro-osteoclastogenic factors seem to increase the ratio of TRANCE/OPG; whereas, anti-osteoclastogenic factors reduce the TRANCE/OPG ratio in osteoblasts. In addition to bone resorbing hormones, inflammatory agents, such as lipopolysaccharide (LPS), also induces the expression of TRANCE while suppressing OPG in osteoblasts. In contrast, inhibitory levels of TGF-β suppress TRANCE expression induced by calciotropic hormones, while enhancing the level of OPG in osteoblasts.

Hence, to determine the potential relationship between LRRc17, OPG and TRANCE expression in osteoblasts when stimulated with various osteotropic factors, the steady-state level of LRRc17 mRNA in osteoblasts was examined by Northern blot analysis in the osteoblastic cell lines E1, PA6 and UAMS-32, as well as in primary calvarial osteoblasts in accordance with the methods described above. The cells were treated with selected osteotropic factors (described below) for a time course evaluated at 0 hrs, 4 hrs, 12 hrs, 24 hrs, 48 hrs, and 72 hrs, and then harvested for RNA preparation.

The duration of stimulation has been determined based upon data produced in response to stimulation with Vit-D3, and because various reports have indicated that both wane and wax stages of mRNA expression can be observed within a period of 3 day stimulation. For example, as shown above, the LRRc17 mRNA level in primary calvarial osteoblasts is rapidly reduced upon Vit-D3 treatment, while the level of LRRc17 mRNA reverts to its baseline after 3 days (FIG. 6). Although it does not fully return to baseline levels, OPG mRNA also comes back after 3 days of Vit-D3 stimulation (FIG. 6; see also Kondo et al., supra, 2004)). Conversely, TGF-β has been shown to up-regulate the OPG mRNA level within 4 hours of stimulation, whereas the reversion to baseline levels occurs after 1-2 days of stimulation (see Thirunavukkarasu et al., supra, 2001).

Among various osteotropic factors evaluated, in addition to Vit-D3, were TNFα (10 ng/ml), IL-1α (10 ng/ml), TGF-β (10 ng/ml), PGE$_2$ (1 µM), testosterone ($10^{-8}$M), estrogen ($10^{-7}$M), PTH ($10^{-8}$M), and LPS (100 ng/ml) because they have been used previously to examine the regulation of OPG and/or TRANCE mRNA expression in various osteoblastic cell lines and primary calvarial osteoblasts as referenced above. As a result, is was determined that the LRRc17 is regulated coordinately with other critical anti-osteoclastogenic factors, such as OPG in osteoblasts, while inversely correlate with that of TRANCE. Although the ultimate relationships may not be that simple, this information further adds to the understanding of the role played by LRRc17 in bone metabolism.

Example 2

Functional analysis of LRRc17 during osteoclast differentiation in vitro. The foregoing determination that osteoclast differentiation is significantly inhibited when cells were used in which LRRc17 is constitutively expressed, was based on two in vitro systems: 1) Vit-D3 induced osteoclastogenesis in the co-culture system with the osteoblastic cell line UAMS-32; and 2) osteoclast differentiation from bone marrow precursors with M-CSF and TRANCE. Although attempts were made to control the expression level of LRRc17 by Northern analysis and by a surrogate marker EGFP, the actual level of LRRc17 protein in the culture could not easily be controlled (as discussed above, LRRc17 is a secreted protein). Thus, a recombinant LRRc17 protein was generated to further test the anti-osteoclastogenic potential of LRRc17.

A. Generation of recombinant LRRc17 protein: Although LRRc17 is putatively a secreted protein, an LRRc17-Fc fusion protein was generated for purposes of the functional analysis for at least two reasons. First, the Fc fusion protein can be easily purified using Protein A. Second, using a fusion protein with the constant region of Ig has been shown to increase protein stability, see for example, previous work reported for the generation of Fc fusion proteins, such as RANK-Fc and OSCAR-Fc (Kim et al., supra, 2002; Bachmann et al., *J. Exp. Med.* 189:1025-1031 (1999), each is herein incorporated by reference).

Figure 9:
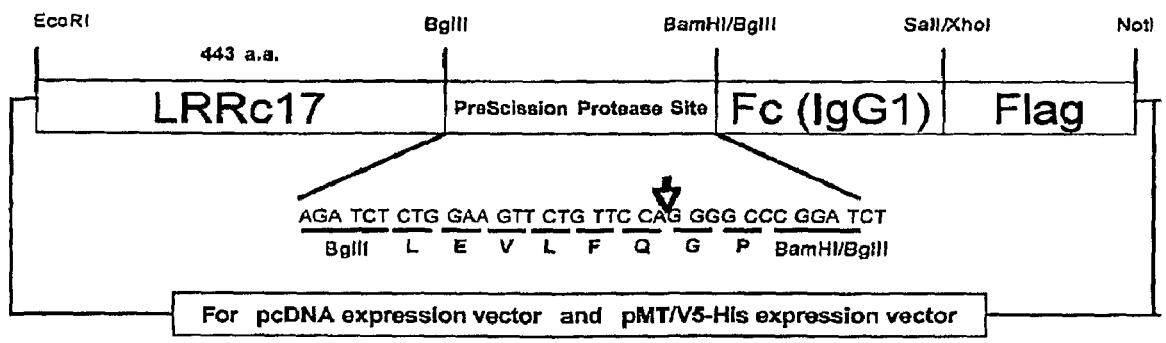
FIG. 9 is a schematic view of the LRRc17-Fc-Flag cDNAs.

In brief, the entire open reading frame of LRRc17 was fused in frame to the constant region of human IgG1 (FIG. 9) as previously done to produce RANK-Fc and OSCAR-Fc (Id), and it has been produced in *E. coli*. Nevertheless, in the event that LRRc17 needed to be purified without the IgG1 constant region, a PreScission protease site was inserted: SEQ ID No:2 for cDNA encoding the amino acid LEVLFQGP (SEQ ID No:3). In addition, a Flag tag was introduced at the carboxyl terminus after the IgG1 constant region as shown in FIG. 9, thus providing an additional way of detecting recombinant LRRc17, as needed to investigate the role of LRRc17 in bone resorption below.

For the insect cell vector system, LRRc17-Fc-Flag cDNA was cloned into pMT/V5-His to yield the expression vector pMT-LRRc17-Fc-Flag, which was co-transfected with (pCo-HYGRO) into *Drosophila* (e.g., Invitrogen, Carlsbad, Calif. offers a DES®-*Drosophila* Expression System using a *Drosophila* metallothionein (MT) or actin 5C promoter and constitutive expression vector, pAc5.1/V5-His; or pMT/BiP/V5-His vector with BiP signal for secreted expression of the LRRc17 gene). pCoBlast or pCoHygro permit for transient or inducible expression (to the appropriate scale) intracellularly or secreted for a simplified purification in a cell line such as S2, selected for hygromycin resistance, expanded, and used for production and purification of the recombinant LRRc17 fusion protein (Id). Once a consistently large supply of purified LRRc17-Fc-Flag fusion protein was obtained, it was used for the functional assays described below.

To test the feasibility of the Fc fusion protein, a transient transfection system was used. In brief, the LRRc17-Fc-Flag fusion protein cDNA (FIG. 9) was cloned into pcDNA, and used to transiently transfect 293T cells according to known methods. After 48 hours, recombinant LRRc17-Fc-Flag was purified from culture supernatants, and subjected to western blot analysis using anti-Flag Antibodies (anti-Flag Ab) (shown in FIG. 10A). As expected, using a single purification over a Protein A Sepharose column, or by immunoprecipitation with anti-Flag Ab, the recombinant LRRc17-Fc-Flag fusion protein (~90 kD was purified, having a core protein of the calculated size ~75 kD, plus glycosylation). Although the amount of purified protein was limited, at least one experiment of functional analysis could be carried out on a pilot scale, but with triplicates for each data point.

Importantly, addition of LRRc17 fusion protein inhibited, in a dose-dependent manner, osteoclast differentiation of bone marrow precursors stimulated with TRANCE and M-CSF (FIG. 10B). This demonstrates the anti-osteoclastogenic properties of LRRc17. Nevertheless, although this transient transfection system is fast, previous experience has shown that it tends not to yield a consistent supply of recombinant protein. Therefore, large-scale preparations of LRRc17-Fc-Flag cDNA can be achieved by using an insect cell expression system as described above.

B. LRRc17 and osteoclast differentiation in vitro: To further confirm the function of LRRc17 as an inhibitor of osteoclast differentiation, three standard in vitro osteoclast differentiation protocols were used:

1) Vit-D3 induced osteoclast differentiation using the co-culture system with primary calvarial osteoblasts and bone marrow precursors: Primary calvarial osteoblasts were obtained from calvarias of newborn C57BL/6 mice by the conventional method using collagenase, and bone marrow cells were obtained from the femors and tibiae of 4- to 7-week-old C57BL/6 male mice (Kim et al., supra, 2002; Suda et al., supra, 1997; Kadono et al, supra, 2005, all incorporated by reference). Calvarial osteoblasts ($1 \times 10^4$ cells) and bone marrow cells ($1 \times 10^5$ cells) were co-cultured in the presence or absence of $10^{-8}$ M Vit-D3 in 0.2 ml aMEM containing 10% FBS in 96-well culture plates. After 5, 6, or 7 days of culture, cells were fixed and stained for TRAP as previously done in the lab (Id). TRAP-positive multinucleated cells were counted as osteoclast-like multinucleated cells (MNCs).

To determine the pit-forming activity of osteoclasts, calvarial osteoblasts ($1 \times 10^4$ cells) and bone marrow cells ($1 \times 10^5$ cells) were co-cultured in the presence or absence of $10^{-8}$M Vit-D3 on bone slices (0.2-0.3 mm in thickness, 4 mm in diameter), and placed in 96-well culture plates for 6 days as described above and by Kim, Suda and Kadono supra. The slices were then be recovered, cleaned by ultrasonication in 0.5 M $NH_4OH$ to remove adherent cells, and stained with Mayer's hematoxylin (Sigma Chemical Co., St. Louis, Mo.) to visualize resorption pits (Id). The number of pits on slices were counted by microscope observation. To test the function of LRRc17, varying doses of purified LRRc17-Fc-Flag protein were added to the culture. Human IgG1 was used as a negative control for exogenous recombinant Fc fusion protein, and RANK-Fc was used as a positive control for inhibition of osteoclast differentiation. Media of each culture was replaced with fresh media every 3 days.

Once the inhibition of osteoclast differentiation by LRRc17-Fc-Flag protein was confirmed in the co-culture system, the next step was to determine whether it was possible to nullify the effect of LRRc17 by administering excessive doses of M-CSF and/or TRANCE. For this, increasing amounts of M-CSF and/or TRANCE were added in conjunction with LRRc17-Fc-Flag at a concentration that gives half-maximal inhibition in the co-culture system. In addition, other osteotropic factors (e.g., PTH, LPS) were included in the co-culture system to examine the role of LRRc17 on osteoblast-mediated osteoclast differentiation. Prioritization of which osteotropic factors were tested, depended on how LRRc17 expression is regulated in osteoblasts by the various factors.

2) Osteoclast differentiation of bone marrow precursors by TRANCE and M-CSF: Osteoclast precursors were prepared as above (Id). In brief, mouse bone marrow cells were cultured in αMEM containing 10% FBS with M-CSF (5 ng/ml) for 12 hrs in 100-mm diameter dishes ($1 \times 10^7$ cells/10 ml/dish) to separate adherent cells and non-adherent cells. Then, non-adherent cells were harvested and cultured with M-CSF (30 ng/ml) in 100-mm diameter dishes ($1 \times 10^7$ cells/10 ml/dish). After 2 days of culture, floating cells will be removed and attached cells will be used as osteoclast precursors.

To generate osteoclast cells, osteoclast precursors were cultured with TRANCE (100 ng/ml) and M-CSF (30 ng/ml) for 3 days in 96-well culture plates ($2 \times 10^4$ cells/0.2 ml/well). Varying amounts of LRRc17-Fc-Flag fusion protein were added with TRANCE (100 ng/ml) and M-CSF (30 ng/ml) for 3 days. The amounts of TRANCE and/or M-CSF used in the culture were titrated down in the presence of a constant amount of LRRc 17 fusion protein, essentially as previously done with OSCAR-Fc (Id). Increasing amounts of TRANCE and/or M-CSF were also added to confirm the nullifying effect of LRRc17 as described above.

3) Osteoclast differentiation of RAW264.7 cell line: To generate osteoclasts from the murine myeloid RAW264.7 cell line, cells will be cultured in 96-well culture plates ($1 \times 10^3$ cells/0.2 ml/well) with TRANCE (100 ng/ml) for 4 days according to the methods above (Id). (RAW264.7 [ATCC TIB 71] is an immortalized, transfectable macrophage cell line isolated from BALB/c mouse clone with the capacity to form osteoclast-like cells). Media was replaced with fresh media containing TRANCE (100 ng/ml) on day 3. Once inhibition of osteoclast differentiation is observed by the recombinant LRRc17-Fc-Flag protein in the RAW264.7 cell line system, increasing doses of TRANCE are used in conjunction with LRRc17-Fc-Flag at a concentration that gives half-maximal inhibition in the RAW264.7 cell line system to determine whether the effect of LRRc17 can be nullified by the excessive doses of TRANCE.

Thus, the foregoing experiments demonstrate that an excessive amount of LRRc17 inhibits osteoclast differentiation, that the level of LRRc17 expression in osteoblasts is suppressed by Vit-D3 treatment, and that the LRRc17 expression pattern correlates with that of OPG, and inversely with that of TRANCE in response to Vit-D3, which when combined confirms that LRRc17 plays an important inhibitory role in osteoclast differentiation. Of course, once the importance of LRRc17 is confirmed for bone homeostasis in vivo, and as an inhibitor of increased osteoclastic bone loss in vivo, particularly under physiological conditions when osteoclastogenesis is induced by osteoblasts in response to various calciotropic factors, it will be an important step toward developing additional therapeutic approaches for various human diseases caused by excessive osteoclast activity.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

We claim:

1. A method of inhibiting osteoclastogenesis comprising contacting osteoclast precursor cells with an LRRc17 protein comprising the amino acid sequence of SEQ ID NO: 1, or an LRRc17 protein variant having an amino acid sequence at least 95% sequence identical to the amino acid sequence of SEQ ID NO: 1, wherein said variant has the activity of negatively regulating osteoclast differentiation.

2. A method of enhancing bone formation, density, and/or mass in a subject in need thereof, comprising administering to the subject a composition comprising an LRRc17 protein comprising the amino acid sequence of SEQ ID NO: 1, or an LRRc17 protein variant having an amino acid sequence at least 95% sequence identical to the amino acid sequence of SEQ ID NO: 1, wherein said variant has the activity of negatively regulating osteoclast differentiation.

3. The method of claim 2, wherein the subject suffers from a disease or disorder selected from the group consisting of: osteoporosis, metastatic cancer in bone of unknown origin, metastatic cancer in bone originating from prostate, metastatic cancer in bone originating from breast, rheumatoid arthritis, osteoarthritis, periodontal disease, prosthetic joint loosening, artificial hip loosening, and a degenerative bone disorder.

4. The method of claim 2, further comprising adjunctively administering an anti-resorptive agent selected from the group consisting of: a bisphosphonate, calcitonin, a calcitonin analog, estrogen, an estrogen analog, and a selective estrogen receptor modulator (SERM).

5. The method of claim 2, further comprising adjunctively administering an osteo-anabolic agent selected from the group consisting of: parathyroid hormone, parathyroid hormone analog, strontium renelate, and growth hormone.

6. A method of inhibiting bone resorption in a subject in need thereof, comprising administering to the subject a composition comprising an LRRc17 protein comprising the amino acid sequence of SEQ ID NO: 1, or an LRRc17 protein variant having an amino acid sequence at least 95% sequence identical to the amino acid sequence of SEQ ID NO: 1, wherein said variant has the activity of negatively regulating osteoclast differentiation.

7. The method of claim 6, wherein the subject suffers from a disease or disorder selected from the group consisting of: osteoporosis, metastatic cancer in bone of unknown origin, metastatic cancer in bone originating from prostate, metastatic cancer in bone originating from breast, rheumatoid arthritis, osteoarthritis, periodontal disease, prosthetic joint loosening, artificial hip loosening, and a degenerative bone disorder.

8. The method of claim 6, further comprising adjunctively administering an anti-resorptive agent selected from the group consisting of a bisphosphonate, calcitonin, a calcitonin analog, estrogen, an estrogen analog, and a selective estrogen receptor modulator (SERM).

9. The method of claim 6, further comprising adjunctively administering an osteo-anabolic agent selected from the group consisting of parathyroid hormone, parathyroid hormone analog, strontium renelate, and growth hormone.

* * * * *